United States Patent [19]

Nathan

[11] Patent Number: 5,871,914
[45] Date of Patent: Feb. 16, 1999

[54] METHOD FOR DETECTING A NUCLEIC ACID INVOLVING THE PRODUCTION OF A TRIGGERING RNA AND TRANSCRIPTION AMPLIFICATION

[75] Inventor: Asher Nathan, Bet-Shemesh, Israel

[73] Assignee: Intelligene Ltd., Israel

[21] Appl. No.: 556,940

[22] PCT Filed: Jun. 2, 1994

[86] PCT No.: PCT/US94/06034

§ 371 Date: Apr. 9, 1996

§ 102(e) Date: Apr. 9, 1996

[87] PCT Pub. No.: WO94/29481

PCT Pub. Date: Dec. 22, 1994

[30] Foreign Application Priority Data

Jun. 3, 1993 [IL] Israel .......................................... 105894

[51] Int. Cl.$^6$ .............................. C12Q 1/68; C12P 19/34; C07H 21/04
[52] U.S. Cl. ............................. 435/6; 435/91.21; 935/17; 935/78; 536/24.33; 536/24.3
[58] Field of Search ........................... 435/91.21, 6, 91.2; 935/77, 78; 536/24.33, 24.3

[56] References Cited

U.S. PATENT DOCUMENTS

| | | | |
|---|---|---|---|
| 5,215,899 | 7/1993 | Dattagupta | 435/6 |
| 5,348,853 | 9/1994 | Wang et al. | 435/6 |
| 5,356,774 | 10/1994 | Axelrod et al. | 435/6 |
| 5,369,003 | 11/1994 | Reischl et al. | 435/6 |
| 5,434,047 | 7/1995 | Arnold, Jr. | 435/6 |
| 5,532,126 | 7/1996 | Chu et al. | 435/6 |

FOREIGN PATENT DOCUMENTS

WO 89/05631 6/1989 France .
WO 89/05533 6/1989 Sweden .

OTHER PUBLICATIONS

Analytical Biochemistry, vol. 208, issued 1993; V. Kohli et al, "Comparison of in Vitro Transcriptions Usi Various Types of DNA Templates", pp. 223–227, see entire document.

Cell, vol. 63, issued 02 Nov. 1990, M.M. Konarska et al., "Structure of RNAs Replicated by the DN Dependent T7RNA Polymerase", pp. 609–618, see entire document.

Gene, vol. 106, issued 1991, S.L. Leary et al., "DNA–dependent RNA Polymerase from Bacteriophage Transcribes and Amplifies an RNA Template in Vitro", pp. 93–96, see entire document.

Proceedings of the Nat. Academy of Sci. USA, vol. 86, issued Feb. 1989, D.Y. Kwoh et al., "Transcription–based amplification system and detection of amplified human immunodeficiency virus type I with a bead–based sandwich hybridization format", pp. 1173–1177, see entire document.

Proceedings of the Nat. Academy of Sciences, USA, vol. 87, issued Mar. 1990, J.C. Guatelli et al, "Isothermal, in vitro, amplification of nucleic acids by a multienzyme reaction modeled after retroviral replication", pp. 1874–1878, see entire document.

(List continued on next page.)

Primary Examiner—Lisa B. Arthur
Attorney, Agent, or Firm—Wigman, Cohen, Leitner & Myers, P.C.

[57] ABSTRACT

A method for detecting the presence of an assayed nucleic acid in a sample is an essentially two-stage procedure. In a first stage the sample is reacted in a manner which gives rise to the production of a triggering RNA where the sample contains the assays sequence. In the second stage, the reaction product is incubated under appropriate conditions with an amplification reagent ensemble whereby, in the presence of triggering RNA a large amount of a nucleic product is obtained. The detection of this product thus indicates the presence of the assayed sequence in the sample.

21 Claims, 16 Drawing Sheets

OTHER PUBLICATIONS

Chetverin, Alexander B. et al., *On the Nature of Spontaneous RNA Synthesis by Qβ Replicase,* J. Mol. Biol. 1991, 222, 3–9.

Nath, Kamalendu et al., *Covalent Attachment of Polyribonucleotides . . . Ligase,* J. Biol. Chem. vol. 219, No. 12, pp. 3680–3688, 1974.

Moore, Melissa J. et al., *Site–Specific Modification of Pre–mRNA . . . Sites,* Science, vol. 256, 1992, pp. 992–997.

Milligan, John F., et al., *Oligonucleotide Synthesis Using . . . Templates,* Nucl. Acids Research, vol. 15, No. 21, 1987, pp. 8783–8798.

Barany, Francis, *Genetic Disease Detection . . . Ligase,* Proc. Natl. Acad. Sci. USA, vol. 88, pp. 188–193, 1991.

METHOD FOR DETECTING A NUCLEIC ACID INVOLVING THE PRODUCTION OF A TRIGGERING RNA AND TRANSCRIPTION AMPLIFICATION

This application was filed under 35 USC 371 from PCT Application PCT/US94/06034.

FIELD OF THE INVENTION

The present invention concerns a method and kit for the detection of specific nucleic acid sequence in a sample.

BACKGROUND OF THE INVENTION

Detection of the presence of a specific DNA or RNA sequence in a sample is required for a variety of experimental, diagnostic and therapeutic purposes, e.g. detection of a specific mutation in a sample of amniotic fluid, parenterage testing, testing for incorporation of a viral DNA into a cell's genomic DNA, etc. The task of direct detection of a specific DNA or RNA sequence, which is routinely performed by the use of an appropriately labelled probe, is often hindered by the fact that the specific DNA or RNA is present in a sample only in minute amounts.

Examples of methods which enable the amplification of DNA sequences present in a sample in only minute quantities are: LCR (ligase chain reaction), 3SR (self-sustained sequence replication) or PCR (polymerase chain-reaction). In PCR a sample is contacted with a primer DNA complimentary to a 3' end sequence of the specific DNA, a DNA polymerase and with single DNA nucleotides. Following a number of replication cycles, the sample is enriched with the specific assayed DNA. A typical cycle of PCR comprises three distinct stages: a first stage in which the double-stranded DNA is melted to two single strands; a second stage of annealing of the primer to the single-stranded DNA; and a third stage of polymerization where the annealed primers are extended by the DNA polymerase, to produce a double-stranded DNA. The cycle of melting, annealing and DNA synthesis is repeated many times, the products of one cycle serving as templates for the next ad thus, each successive cycle enriches the sample with the specific DNA.

PCR suffers from several shortcomings, the most serious of which being its lack of specificity. The effective hybridization temperature, i.e. the temperature in which the two strands of DNA hybridize, determines the specificity of the reaction. A low effective hybridization temperature results in a higher percentage of non-specific binding. In PCR this temperature, which is defined by the temperature of the annealing stage, is relatively low and this brings about non-specific binding of the probe to the target sequences resulting in amplification of undesired sequences which brings about a relatively high background reading.

This non-specificity also requires an additional and time-consuming detection procedure such as electrophoretic separation of the amplification products on an agarose gel, in order to separate between the various amplification products, and does not enable detection of the presence of the assayed DNA by a mere detection of amplification.

PCR also suffers from a severe problem of contamination which is due to amplification of sequences that did not originate from the test sample being sequences unintentionally introduced to the sample.

Another disadvantage of PCR is that it is a complex procedure. Typically, each of the stages of melting, annealing and polymerization is carried out at a different temperature, e.g. melting at 94° C., annealing at 50° C. and polymerization at 72° C. Since the samples have to be constantly cycled through several temperatures a special apparatus is required rendering the procedure laborious and time consuming.

Another shortcoming of PCR is in the time required therefor. A typical cycle lasts several minutes, and usually 25–30 cycles are required to produce sufficient copies of amplified DNA. Thus, a typical PCR even in a completely automated system lasts at least 2 to 3 hours.

Finally, PCR is basically suited for the detection of DNA sequences. Where detection of RNA sequences is desired, RNA has to be converted first to DNA (by reverse transcription). This conversion to DNA requires additional time, effort and enzymes, and also introduces many errors due to the inherent inaccuracy of reverse transcription.

It should be noted that although PCR is advantageous in obtaining large amounts of a specific DNA, such as for producing large quantities of probes for genetic assays, it is often an "over-kill" where merely the presence of a specific DNA sequence in a sample is to be assayed.

Other such methods such as 3SR (WO PCT 89/05631) and Target Nucleic Acid Amplification/Detection (WO PCT 89/05533) are relatively rapid isothermal processes for DNA detection. However, these methods also suffer from relatively effective low hybridization temperatures which are even lower than those of PCR, typically in the range of 37°–41° C. These low temperatures drastically reduce the specificity of the procedure due to non-specific probe-target binding, and in cases of clinical diagnostics, this may result in an intolerable level of misdiagnosis.

Additionally, amplification strategies such as Target Nucleic Acid Amplification/Detection that are based on the amplification properties of a replicase-type enzyme are unreliable due to the possibility of spontaneous RNA amplification in the absence of target (Chetverin-AB, et al., *J. Mol. Biol.*, 222(1), 3–9 (1991)).

It is the object of the invention to provide a method for the detection of a nucleic acid sequence which is:

(i) reliable and sequence specific due to the minimalization of incorrect target-probe hybridization;
(ii) relatively rapid;
(iii) essentially isothermic eliminating the need for specialized and expensive apparatus;
(iv) relatively simple, not requiring the addition of a large number of different enzymes or nucleotide pools; and
(v) amenable to automation by enabling the amplification process itself to be indicative of the presence or absence of the nucleic acid sequence to be assayed.

Further objects of the invention will become clear from the following description.

GLOSSARY

Below are the meanings of some of the terms which will be used in the following description and claims. For ease of reference, the reader is also referred to the accompanying drawings (the numbers in brackets in the Glossary below refer to the item numbers in the drawings):

Assayed nucleic acid sequence (102,202,302,402,502,602, 1402)

The DNA or RNA sequence which presence in the sample is to be detected.

First DNA molecule (220,320,420,520,620,1420)

a DNA molecule having a double-stranded, i.e. functional promoter and a 5' end sequence which is complementary to the 5' end portion of the assayed nucleic acid sequence (102, . . . etc.).

Second DNA molecule (222,322,432,522,622,1422)

a DNA molecule comprising a single-stranded 3' end sequence being complementary to the 3' end portion of the assayed nucleic acid sequence (102, . . . etc.) and further comprising a sequence which can be transcribed to the triggering RNA sequence (see below). The 3' end sequence of the second DNA molecule and the 5' end sequence of the first DNA molecule may be complementary to the entire assayed nucleic acid sequence or to only a part thereof, leaving an intermediary portion in the assayed nucleic acid sequence having no complementary counterparts in either the first or second DNA molecules.

Third DNA molecule (623)

a single-stranded DNA molecule complementary to the intermediary portion of the assayed nucleic acid sequence.

Detection ensemble (104,204)

an ensemble of molecules comprising the first DNA molecule (220, . . . etc.), the second DNA molecule (222, . . . etc.), and where the 5' end sequence and the 3' end sequence of the first and second DNA molecule, respectively, are complementary together to only a portion of the assayed nucleic acid sequence also comprising the third DNA molecule (623). The detection ensemble optionally comprises also a ligase. In the presence of the assayed DNA (102, . . . etc.) and the transcription reagents (see below) the detection ensemble is activated and an RNA transcript (110,210,310,410,510,610,710,810,910,1010, 1110,1210,1310, 1410,1510,1610) comprising the triggering RNA sequence (see below) is produced.

Triggering RNA sequence a sequence in the RNA transcript (110, . . . etc.) transcribed from the second DNA molecule (222, . . . etc.), which is only produced after activation of the detection ensemble. This RNA sequence is then capable of triggering transcription in the RNA amplification ensemble (see below) of a signal RNA molecule (see below) comprising the signal RNA sequence (see below).

Triggering RNA molecule (110,210,310,410,510,610,710, 810,910,1010, 1110,1210,1310,1410,1510,1610)

the RNA molecule comprising the triggering RNA sequence.

Signal RNA sequence a sequence in the transcription product of the RNA amplification ensemble (see below). The production of the signal RNA sequence, above a baseline level, indicates the presence of the assayed nucleic acid sequence in the sample.

Signal RNA molecule (116,716,816,916,1016,1116,1216)

the RNA molecule comprising the signal RNA sequence.

Signal DNA sequence a DNA sequence serving as a template from which the signal RNA sequence is transcribed.

Transcription reagents (113,213,413,513,713,813,913,1013, 1113,1213, 1313,1413,1513,1613)

RNA polymerase with single RNA nucleotides and buffers required for RNA transcription.

Transcription system a DNA homoduplex or a DNA/RNA heteroduplex comprising a functional promoter and a downstream DNA or RNA sequence which can be transcribed upon activation of the promoter into an RNA transcript.

RNA amplification ensemble (FIGS. 7–13, 15,16)

an ensemble comprising essentially the triggering RNA molecule (110, . . . etc.) and the transcription reagents (213, . . . etc.) in the first embodiment of the invention; or the triggering RNA molecule (116, . . . etc.), the transcription reagents (213, . . . etc.) and fourth DNA molecule (see below) in the second embodiment; or the triggering RNA, the transcription reagents and a fifth and sixth DNA molecules (see below), in the third embodiment of the invention; or the triggering RNA, the transcription reagents, and a seventh and eighth DNA molecule in the fourth embodiment of the invention. The RNA amplification ensemble optionally comprises a ligase. In one embodiment of the first embodiment, the presence of the triggering RNA together with the transcription system is sufficient for the transcription of the signal RNA sequence. In the second embodiment, the triggering RNA hybridizes with the fourth DNA molecule. In the third embodiment, the triggering RNA hybridizes with the fifth and sixth DNA molecules bringing them together. In the fourth embodiment the triggering RNA hybridizes with the seventh or eighth DNA molecules. The RNA/DNA hybrid produced in accordance with the second, third and fourth embodiments, serves as a template for the production of the signal RNA sequence.

Fourth DNA molecule a DNA molecule (1148) which is part of the RNA amplification ensemble in accordance with the second embodiment. This molecule comprises a promoter which is single-stranded in at least an essential part thereof and is thus inactive. It further comprises the signal DNA sequence. When the triggering RNA sequence, which in this embodiment is complementary to the single-stranded part of the promoter, hybridizes with the single-stranded part of the promoter of the fourth DNA molecule, a functional promoter is produced and thus the signal RNA molecule can be transcribed.

Fifth DNA molecule a molecule (1252) which is part of the amplification ensemble in accordance with the third embodiment. It comprises a functional promoter, and at its 5' end, a single-stranded sequence which is complementary to the 5' end portion of the triggering RNA sequence.

Sixth DNA molecule a molecule (1259) which is part of the amplification ensemble in accordance with the third embodiment. It comprises at its 3' end a single-stranded sequence which is complementary to the remaining 3' end portion of the triggering RNA sequence and in addition, comprises the signal DNA sequence.

Seventh DNA molecule a molecule (1580) which is part of the amplification ensemble in accordance with the fourth embodiment. It has a functional, double-stranded promoter, either a priori prepared or assembled from two single stranded sequences, linked to an antisense sequence complementary to the 3' end sequence of the triggering RNA. One or a few end nucleotides in the 5' end of the template strand of this molecule could be RNA nucleotides. The 3' end sequence of the triggering RNA hybridizes to said antisense sequence and after ligation the promoter can induce RNA transcription, the triggering RNA serving as a template.

Eighth DNA molecule a molecule (1529') which is part of the amplification ensemble in accordance with the fourth embodiment. It is similar to the seventh DNA molecule, the difference being in the antisense sequence which in the eighth DNA molecule is identical to the 5' end sequence of the triggering RNA molecule. The transcription product of the seventh DNA molecule/triggering RNA hybrid can thus hybridize to the eighth molecule and the so formed hybrid serves there as a template for transcription of RNA molecule having the sequence of the triggering RNA sequence, which in turn can activate again the seventh DNA molecule in a "ping-pong" manner.

Promoter molecule a DNA molecule (1429) which is part of the detection ensemble according to the fourth embodiment of the invention and is essentially identical to the eighth DNA molecule.

Adapter molecule a DNA molecule (1431) comprising a sequence complementary to the non-template sequence immediately adjacent the promoter sequence in the promoter molecule possibly having one or a few RNA nucleotides at its 3' end.

Joiner molecule a DNA molecule (1433) comprising at its 5' end a sequence which is complementary to a 5' end portion of the adapter molecule and a sequence in the remaining 3' portion of the molecule which is complementary to 3' end portion of the first molecule in accordance with the fourth embodiment. The joiner molecule serves for joining the first and the adapter molecule in the fourth embodiment.

DNA iniation sequence (DIS)

a DNA sequence present downstream of the promoter of the seventh or eighth DNA molecules which enhances transcription of the sequence present downstream therefrom, by the RNA polymerase.

SUMMARY OF THE INVENTION

The present invention is based on a novel concept for the detection of a nucleic acid sequence present in a sample (assayed nucleic acid). The present invention is useful for the detection of a nucleic acid sequence which may be DNA or RNA having a known sequence. The method is based on a system comprising two components: a detection ensemble and an RNA amplification ensemble.

If the assayed nucleic acid sequence is present in the sample, the detection ensemble gives rise to the production of a triggering RNA sequence. The triggering RNA sequence can initiate an RNA amplification reaction in the RNA amplification ensemble, to produce a signal RNA sequence, which can then be detected by means known per se. If the assayed DNA sequence is not present in the sample, the triggering RNA sequence and consequently the signal RNA sequence are not produced. Thus, the presence or absence of the signal RNA sequence indicates the presence or absence, respectively, of the assayed DNA sequence in the sample.

As can be seen, the presence of the assayed sequence is only required for the first step, in the initial detection ensemble and is no longer required for the RNA amplification ensemble. This uncoupling of the detection and amplification steps allows for various manipulations of the detection ensemble such as addition of blocker molecules and the raising of temperatures, which reduces non-specific hybridization. For example, after hybridization, the temperature may be raised once to a temperature in which all non-specific hybrids will melt and only the specific hybrid will remain. All said manipulations have to be carried out only once, during the detection stage, and the cycles of amplification do not require any intervention and can thus be easily automized.

Furthermore, the detection of the presence of the assayed nucleic acid sequence results in RNA amplification which may for example, be detected by light absorbance at a frequency of 260 nm, with no need to open the reaction vessel and separate the various amplification products. The detection of RNA amplification per se obviating the need to determine whether a specific amplification product is present in the reaction mixture considerably simplifies the whole process as well as eliminates contamination of other reaction vessels by aerosol particles from the assayed reaction vessel which is a current problem encountered in other amplification procedures.

In accordance with the present invention, there is no need to amplify the assayed DNA sequence, but rather its presence brings about production of large quantities of the signal RNA sequence. The method of the invention thus involves production and amplification of RNA rather than amplification of DNA as in PCR. Consequently there is no need for melting of the two DNA strands during amplification cycles since the RNA removal from its template occurs during the normal course of transcription, and accordingly the repetitive temperature cycles of PCR are avoided.

Another advantage of the method of the invention is that, contrary to DNA replication, in RNA transcription several RNA polymerase enzymes can operate on the same template simultaneously and thus the overall transcription process is relatively rapid. Furthermore, the speed of RNA production can be increased if the RNA molecule produced in the amplification ensemble and which comprises the signal RNA sequence, comprises also the triggering RNA sequence itself, which triggering sequence can in turn activate additional transcription in a self-amplifying manner, and thereby the production of RNA advances exponentially in a very rapid manner.

Thus, the method of the invention provides a relatively specific, rapid and uncomplicated method for the detection of an assayed nucleic acid sequence in a sample.

The present invention provides a method for detecting the presence of an assayed nucleic acid sequence in a sample, comprising the steps of:

(a) reacting the sample with a detection ensemble comprising:

a first DNA molecule having a promoter sequence and a 5' end sequence which is complementary to the 5' end portion of the assayed nucleic acid sequence;

a second DNA molecule comprising a single-stranded 3' end sequence being complementary to a 3' end portion of the assayed nucleic acid sequence, and further comprising a sequence which can be transcribed into a triggering RNA sequence capable of initiating a reaction in an appropriate transcription system in which an RNA molecule having a signal RNA sequence is being produced; the 3' end sequence of the second DNA molecule and the 5' end sequence of the first DNA molecule may be complementary to the entire assayed nucleic acid sequence or to only a part thereof leaving an intermediary portion in the assayed nucleic acid having no complementary counterpart in either the first or the second DNA molecules, in which case the detection ensemble further comprises a third DNA sequence being complementary to said intermediate portion;

(b) incubating under conditions to allow hybridization of said first DNA molecule and said second DNA molecule and were present also said third DNA molecule with said assayed nucleic acid sequence, and optionally adding a ligase to allow ligation of adjacent ends of said first, second and third DNA molecules;

(c) adding transcription reagents comprising an RNA polymerase and RNA nucleotides and incubating under conditions to allow the formation of RNA transcripts having said triggering RNA sequence;

(d) contacting the RNA transcripts with an RNA amplification ensemble in which the triggering RNA sequence induces formation of RNA molecules containing the signal RNA sequence; and (e) detecting the presence of said signal RNA sequence, positive results indicating the presence of said assayed nucleic acid sequence in said sample.

Said first molecule may comprise a double-stranded and hence functional promoter. Alternatively, the promoter is a priori single-stranded in at least an essential part thereof and a sequence complementary to the single-stranded portion of the promoter is added during or after step (b). Namely, it should be understood that by the above definition of first DNA molecule, the functional promoter may be present a priori or may be assembled in situ during the performance of the assay in the assay vessel.

Steps (a) and (b) of the method of the invention may be modified to increase the specificity of the detection and/or prevent production of short sequences of RNA transcribed from the first DNA molecule, which may increase the background signal. These modifications include, for example, an additional step after step (b) of raising the temperature to a point where only perfectly matched hybrids of assayed nucleic acid sequences and first and second DNA molecules (and also third DNA molecule if present) remain hybridized while all other hybrids in which the individual strands do not perfectly match one another are melted. The reformation of mismatched hybrids after melting can be prevented by the addition of blocker molecules which compete with the assayed nucleic sequence by hybridizing at a high affinity to the first or to the second DNA molecules. Such a modification ensures that triggering RNA is produced only in case of a perfect match between the assayed nucleic acid sequence and the first and second DNA molecules.

In order to avoid production of undesired short RNA transcripts from the first DNA molecule which would have an effect of increasing assay "noise", it is possible to assemble the promoter of the first DNA molecules in stages. In this case, the first molecule comprises a promoter which is single-stranded in at least an essential part thereof and thus non-functional. After the formation of hybrids of the assayed nucleic acid sequence and the first and second DNA molecules, blocker DNA or RNA molecules are added which hybridize only to the free first DNA molecules in such a manner so as to avoid subsequent hybridization thereto of the missing promoter part and cannot hybridize to first DNA molecules present in the hybrid. A DNA molecule comprising the missing promoter part is then added, which completes only the promoter of first DNA molecule in said hybrid rendering it functional and thus enabling the production of the triggering RNA. In contrast to this, the molecule comprising the missing promoter is unable to hybridize with free first DNA molecules which are blocked, and thus no short RNA transcripts are produced from free first DNA molecules.

Free first DNA molecules can also be separated from hybrids of assayed nucleotides and first and second DNA molecules, for example, by having the second DNA molecules bound to a solid support, e.g., magnetic beads and thus, after hybridization, removing all non-bound, i.e. free, DNA molecules.

If the production of short RNA transcripts from the sample is avoided, it is possible to detect the presence of the assayed nucleic acid sequence by detecting the mere amplification of RNA per se, for example, by a change in the absorbance, with no need for the detection of the presence of a specific signal sequence.

Finally, it is possible to determine whether the only transcript produced is a short transcript transcribed from the first DNA molecule or whether in addition, triggering RNA is produced by using synthetic, nucleotides labeled with a fluorescent moiety. One type of these non-naturally occurring nucleotides which are recognized by the RNA polymerase, may be introduced in the coding region first DNA molecule, and a second type may be introduced in the second DNA molecule. The synthetic nucleotides complementary to those present in the first DNA molecule are labeled with one type of fluorescent, i.e. yellow. The synthetic nucleotides complementary to these present in the second DNA molecule are labeled by another type of fluorescent, i.e. blue. After the reaction takes place, the free synthetic nucleotides are separated from the reaction mixture, for example by washing through a charged filter through which the neutral synthetic nucleotides pass. If only short RNA transcripts from the first DNA molecule are produced the fluorescence in the reaction mixture will be totally yellow. If triggering RNA transcriged from both the first and second RNA molecules is produced the fluorescence will be both yellow and blue and will be seen as a green color.

In accordance with a first embodiment of the present invention, the triggering RNA sequence comprises a sequence which can bring about, directly or by hybridizing to various DNA molecules, the production of self-replicating RNA, namely an RNA which serves as a template for formation of identical RNA molecules by an RNA polymerase. Examples of such self-replicating RNA's are X-RNA and Y-RNA (Konarska, MM., Sher, P. A., *Cell*, 63(3), 608–18, (1990). In accordance with the first embodiment, the RNA amplification ensemble, comprises RNA nucleotides and an RNA polymerase and at times DNA molecules which are required in some embodiments for assembling a functional promoter. The signal RNA which is produced in the RNA amplification ensemble is a self-replicating RNA. The presence of self-replicating RNA in the sample, in accordance with the first embodiment, indicates the presence of the assayed DNA sequence in the sample.

In accordance with a second embodiment of the present invention, the amplification ensemble comprises a fourth DNA molecule, which comprises a promoter which is single-stranded in at least an essential part thereof, and is thus inactive, and further comprises a signal DNA sequence which is transcribed into the signal RNA sequence. In accordance with this embodiment, the triggering RNA sequence is complementary to the essential, single-stranded portion of the promoter. When the triggering RNA sequence is contacted with the fourth DNA molecule, the two molecules hybridize whereby the promoter becomes double-stranded and thus functional. Consequently, in the presence of a transcription system, i.e. RNA polymerase and RNA nucleotides, an RNA molecule including the signal RNA sequence is transcribed. Preferably, the RNA molecule thus produced which includes the signal RNA sequence includes also the triggering RNA sequence and consequently the process is self-amplifying, namely, the RNA transcripts produced themselves induce by themselves transcription of additional RNA transcripts.

In accordance with a third embodiment of the invention, the amplification ensemble comprises a fifth DNA molecule which has a functional promoter and a single-stranded sequence at its 5' end and comprises a sixth DNA molecule which has a 3' single-stranded end sequence. The triggering RNA sequence is complementary to the above-mentioned mentioned two single-stranded sequences, its 5' end sequence is complementary to the 5' end sequence of the fifth DNA molecule and its remaining 3' end sequence is complementary to the 3' end sequence of the sixth DNA molecule. Consequently, the triggering RNA sequence after hybridizing to the single-stranded sequence of the fifth DNA molecule and the sixth DNA molecule, brings the respective 5' and 3' ends of the fifth and sixth DNA molecules together whereupon they can be ligated by the use of the ligase. In the presence of an RNA transcription system an RNA transcript comprising a signal RNA sequence is produced. Similarly as in the second embodiment, the fifth DNA molecule optionally comprises a sequence which transcribes into the triggering RNA sequence and the RNA transcript produced therefrom serves also as a trigger for production of additional such transcripts.

By a modification of the third embodiment, the sixth DNA molecule serves as a template for transcription of a self-replicating RNA, such as the X-RNA. Once a self-replicating RNA is produced, it serves as a template for production of further self-replicating RNA molecules.

In accordance with a fourth embodiment of the invention, the amplification ensemble comprises a seventh and an eighth DNA molecule both of which have a functional, double-stranded promoter. The promoters may be, a priori double-stranded or may be assembled in steps from a single-stranded promoter. The seventh DNA molecule has an antisense sequence attached to the non template strand of the promoter which is complementary to the 3' end sequence of the triggering RNA. The eighth DNA molecule has an antisense sequence attached to the promoter which is identical to the 5' end sequence of the triggering RNA. When the triggering RNA is contacted with the amplification ensemble in accordance with the fourth embodiment, the RNA hybridizes to the short antisense sequence in the seventh DNA molecule and after ligation the functional promoter can induce production of RNA, wherein the triggering RNA can serve as template. The RNA transcript thus produced can in turn hybridize in a similar manner to the eighth DNA molecule and the RNA transcript which is produced there is identical to the triggering RNA and can again activate the seventh DNA molecule. Consequently there is a continuous cross-triggering of RNA transcription and a large number of copies of both the triggering RNA and the antisense RNA thereto are produced, which can both serve as the signal RNA.

If desired, it is possible to construct a promoter made of a single DNA strand which is able to loop and form a double-stranded part only under proper conditions. When the promoter is not ligated to the RNA transcript, the loop and hence the double-stranded part is not formed. Only when the promoter is ligated to the RNA transcript the loop structure is stabilized and a double-stranded, functional promoter is formed.

In accordance with a slight modification of the fourth embodiment, it has been found that it is preferable to insert after the promoter a short DNA initiation sequence (DIS) which is recognized at a high affinity by the RNA polymerase and this increases considerably the transcription rate of the RNA molecule (Milligan et al., NAR, 15, pp. 8783 (1987)). One variant of DIS termed "DIS1" should be inserted after the promoter of the seventh molecule and another variant of DIS termed "DIS2" should be added after the promoter of the eighth molecule. Since the DIS is added after the promoter, it becomes transcribed to the RNA molecule in each cycle of amplification so that the transcribed RNA molecules becomes gradually enriched with DIS1 or DIS2 on both ends and then the amplification process is stopped after two cycles. In order to avoid this lengthening phenomena, a rybozyme, which is an RNA sequence featuring catalytic properties and capable of recognizing and cutting a specific RNA sequences, is introduced to the reaction mixture. One type of rybozyme specifically cuts out the RNA sequences transcribed from DIS1 and another rybozyme specifically cuts out DIS2 after each amplification cycle. The sequence transcribed from either DIS, termed hereinafter "dis1" and "dis2" may be cut immediately after transcription when they are on the 5' end, or before hybridization of the triggering RNA to its cognate promoter when it is on the 3'. The latter option has some advantages. First higher fidelity at the 3' end. Since the 3' fidelity of the polymerase is not high, the cutting off the 3' end of the transcript eliminates this problem. Another advantage resides in the fact that cutting by the rybozyme becomes a prerequisite for ligation which ensures the correct sequence of events.

In addition to the advantages stated above, the use of rybozymes in general offers several advantages: first it enables higher specificy. The recognition sequence of the rybozyme can be made highly specific so that after each amplification cycle the specificity of the RNA molecule is verified, thereby reducing background noise due to contamination of the reaction by undesired nucleic acid molecules.

Second, rybozymes can replace the need for a ligase. Some rybozymes are able to specifically ligate two RNA molecules together, so that the nick that occurs after the triggering transcript anneals to its promoter can be repaired by the rybozyme instead of enzymatically.

Third, improved read-out strategies. There is a wide repertoire of rybozyme enzymatic activies. Some rybozymes are able to add a single nucleotide to the RNA sequence and some are able to cut a single nucleotide therefrom, for example, during the ligation procedure. By using labeled nucletides these properties of the rybozymes can be used to ease detection of the transcription products.

The present invention also provides a kit for carrying out the method of the invention. The kit typically comprises the various DNA molecules, reagent systems, etc. required for carrying it out. Separate kits for each of the above-mentioned embodiments are provided.

The invention will now be illustrated with reference to some non-limiting specific embodiments described in the following with occasional reference to the annexed drawings.

Figure 1:
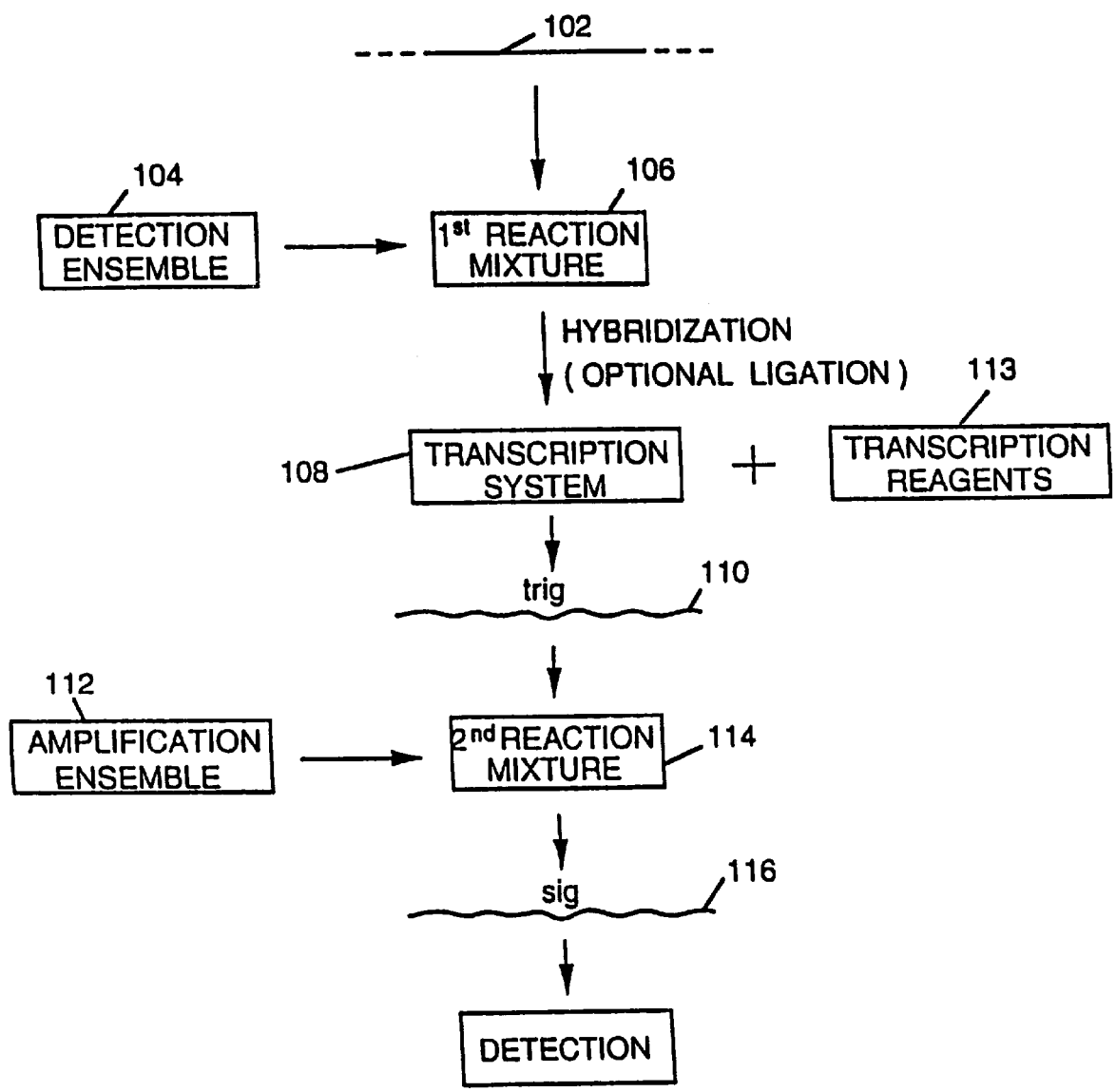
FIG. 1 shows a flow chart of the method of the invention.

In the drawings, various symbols are used which in the context of the present description have the following meanings:

Straight line (_____) - DNA strand
Wavy line (⁓) - RNA strand
A,B,C, etc. - sequences in the coding strand of a DNA
A',B',C', etc. - complementary sequences in non-coding DNA strands
a',b'c', etc. - sequences in RNA transcribed from DNA sequences A,B,C, etc.
a,b,c, etc. - sequences in RNA complementary to a',b',c', etc.
A",B" - sequences in DNA which are partially complementary to DNA sequences A and B
TRIG - triggering DNA sequence
trig - triggering RNA sequence
SIG - signal DNA sequence
sig - signal RNA sequence
P$^+$ - functional promoter (DNA)
P$^-$ - non-functional promoter (DNA)
p$^+$ - functional promoter (RNA)
p$^-$ - non-functional promoter (RNA)
A-α,B-β,A'-α',B'-β',C-γ etc. - complementary sequences on the same strand of nucleic acid sequence
DIS$^-$ - DNA initiation sequence In the figures, the various components are designed by three or four digit numerals. The first digit in a case of a three digit numeral and the first two digits in the case of a four digit numeral represent the figure number and the last two digits represent the component number. In all figures like components have the same component number. Thus, for example, a component 852 in FIG. 8 has the same function as 1052 in FIG. 10, etc.

METHOD OVERVIEW

Reference is first made to FIG. 1 showing an overview of the method of the present invention. Nucleic acid sequence 102 which is in this example a DNA sequence, forming part of a genome of an organism in an assayed sample, is contacted with a detection ensemble 104, comprising various DNA molecules (as will be elaborated further below) to form a first reaction mixture 106. The reaction mixture is subjected to conditions allowing a hybridization of the assayed sequence 102 with corresponding sequences in the DNA molecules of the detection ensemble (see further below).

Following hybridization and optional ligation steps, a transcription system 108 is obtained comprising a DNA heteroduplex having a double-stranded, i.e. functional promoter and a downstream DNA sequence which can be transcribed into an RNA molecule 110 which is referred to herein as the triggering RNA molecule. In order to obtain the triggering RNA molecule 110, transcription reagents 113 comprising RNA polymerase and single RNA nucleotides are added to the transcription system 108.

The triggering RNA molecule is then combined with an amplification ensemble 112 to yield a second reaction mixture 114. The amplification ensemble comprises reagents which in the presence of the triggering RNA sequence will give rise to the production of large quantities of an RNA molecule 116, referred to herein as the signal RNA molecule. The detection of the presence of the signal RNA molecule can then be carried out by any number of means known per se.

In the following, various features of the invention will be described with reference to some specific embodiments. FIGS. 3–6 and 14 describe various embodiments and modifications of the detection ensemble shown in FIG. 2. FIGS. 7–13 and 15, 16 show various embodiments of the amplification ensemble and the production of the signal RNA molecule.

DETECTION ENSEMBLE

Figure 2:
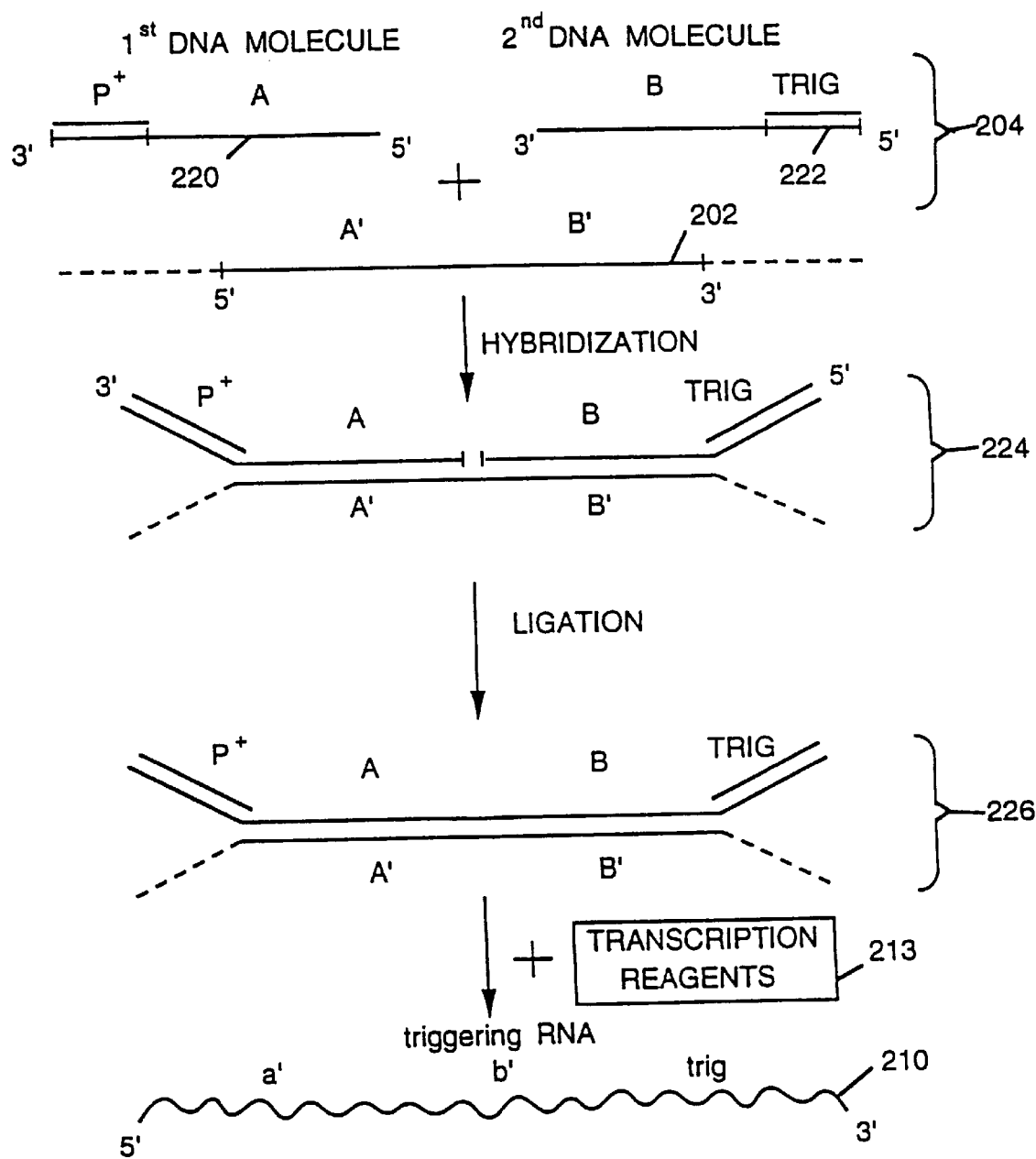
FIG. 2 shows the basic components of the detection ensemble.

Reference is first made to FIG. 2 showing the basic features of the first step in the performance of the method of the invention in which the triggering RNA sequence is produced. From here on the invention will be described with reference to the embodiments in which the assayed nucleic acid sequence in a DNA sequence and it is to be understood that the method is applicable also to RNA sequences, mutatis mutandis.

The detection ensemble 204 comprises a first DNA molecule 220 and a second DNA molecule 222. The first DNA molecule 220 comprises a functional, double-stranded promoter P$^+$. The first DNA molecule 220 has a single-stranded sequence A and the second DNA molecule has a single-stranded sequence B linked to a triggering sequence TRIG which may be single or double-stranded. The sequences A and B are complementary to sequences A' and B', respectively, in the assayed DNA 202.

If the assayed DNA 202 is present in the sample, and appropriate conditions for hybridization are provided, a hybrid 224 is produced. In this hybrid the 3' end of sequence B and the 5' end of sequence A are adjacent to one another and are optionally ligated to yield ligation product 226.

Transcription reagents 213 comprising RNA polymerase such as the T7 polymerase and RNA nucleotides and buffers are then added and as a result a triggering RNA molecule 210 having a triggering sequence - trig linked to sequence b' and a' is produced.

Figure 3:
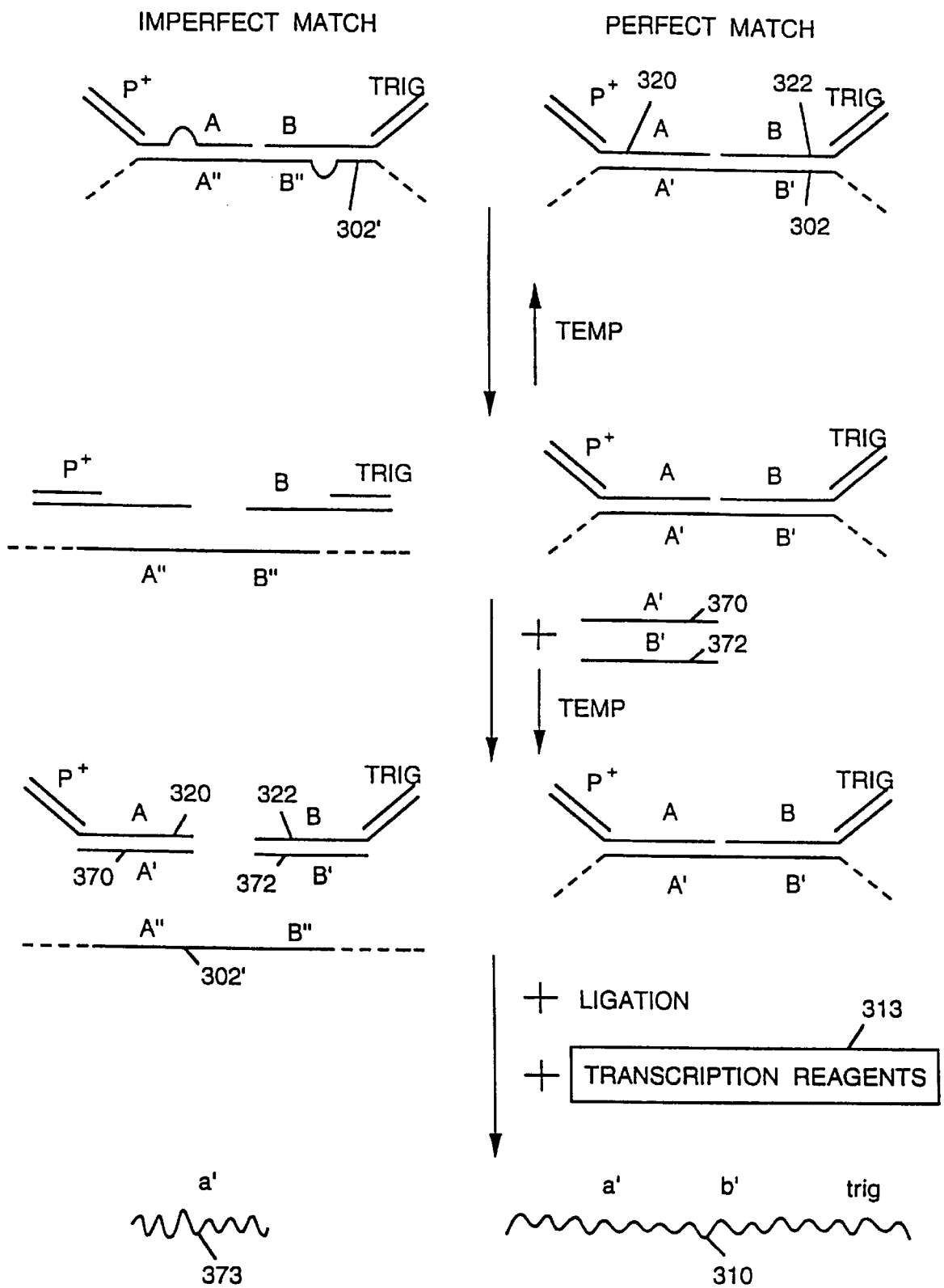
FIG. 3 shows a modification of the method outlined in FIG. 2 intended to decrease the likelihood of a positive result in the case of an imperfect match between the detection ensemble and the assayed DNA.

Reference is now made to FIG. 3 showing a modification of the method outlined in FIG. 2 intended to eliminate almost entirely the possibility of obtaining a positive result in case of an imperfect match between the detection ensemble and the assayed DNA. The right-hand side of FIG. 3 shows the case of a perfect match between the first 320 and second 322 DNA molecules and the assayed DNA 302; and the left-hand side of the figure shows the case of an imperfect match, where the assayed DNA 302' comprises sequences A" and B" (the mismatch being represented schematically by loops in sequence A and sequence B").

After hybridization between the DNA sequences, as described in connection with FIG. 2, the temperature is raised to a temperature wherein there will be a total melting of the DNA sequences in case of an imperfect match and less than total melting, e.g. 50%, in case of a perfect match. This temperature depends, as known, on a number of factors including the length of the DNA sequences as well as the relative proportion of the nucleotide bases A and T versus G and C, and has to be determined empirically in each case.

At this temperature short DNA fragrance 370 and 372 having sequences A' and B', respectively, are added which hybridize to the single-stranded A and B sequences. The temperature is then lowered and a ligase and transcription reagents are then added. In the case of an imperfect match, only small RNA transcripts 373 with the sequence a' will be produced whereas in the case of a perfect match, an RNA transcript 310 having the triggering RNA sequence - trig will be produced.

A In case there is a significant difference between melting temperatures of the above two hybrids, for example, where the hybrid in the case of any imperfect match between the first DNA molecule and the assayed DNA has a melting temperature $T_1$ which is higher than melting temperature $T_2$ of the hybrid containing the second DNA molecule, the method may proceed as follows: addition of first DNA molecule 320 and second DNA molecule 322; addition of blocker molecule 370; raising temperature to $T_1$; lowering temperature to $T_2$; addition of blocker molecule 372; lowering temperature to reaction temperature; addition of transcription reagents 313.

In order to ensure that the blocker molecules 370 and 372 have an advantage over the mismatched assayed DNA in re-hybridization with the first and second DNA molecule when the temperature is lowered, these blocker molecules should be in excess to the assayed DNA. In addition, it is possible to add an extra orbitrary sequence to first molecule 320 and to add a sequence complementary to said extra sequence, to blocker molecule 370. This extra sequence raises the affinity between the blocker molecule and the first DNA molecule to be higher than the affinity between the first DNA molecule and the mismatched portion of the assayed DNA. An extra orbitrary sequence can be added in a similar manner, to second DNA molecule and blocker molecule 372 respectively.

Figure 4:
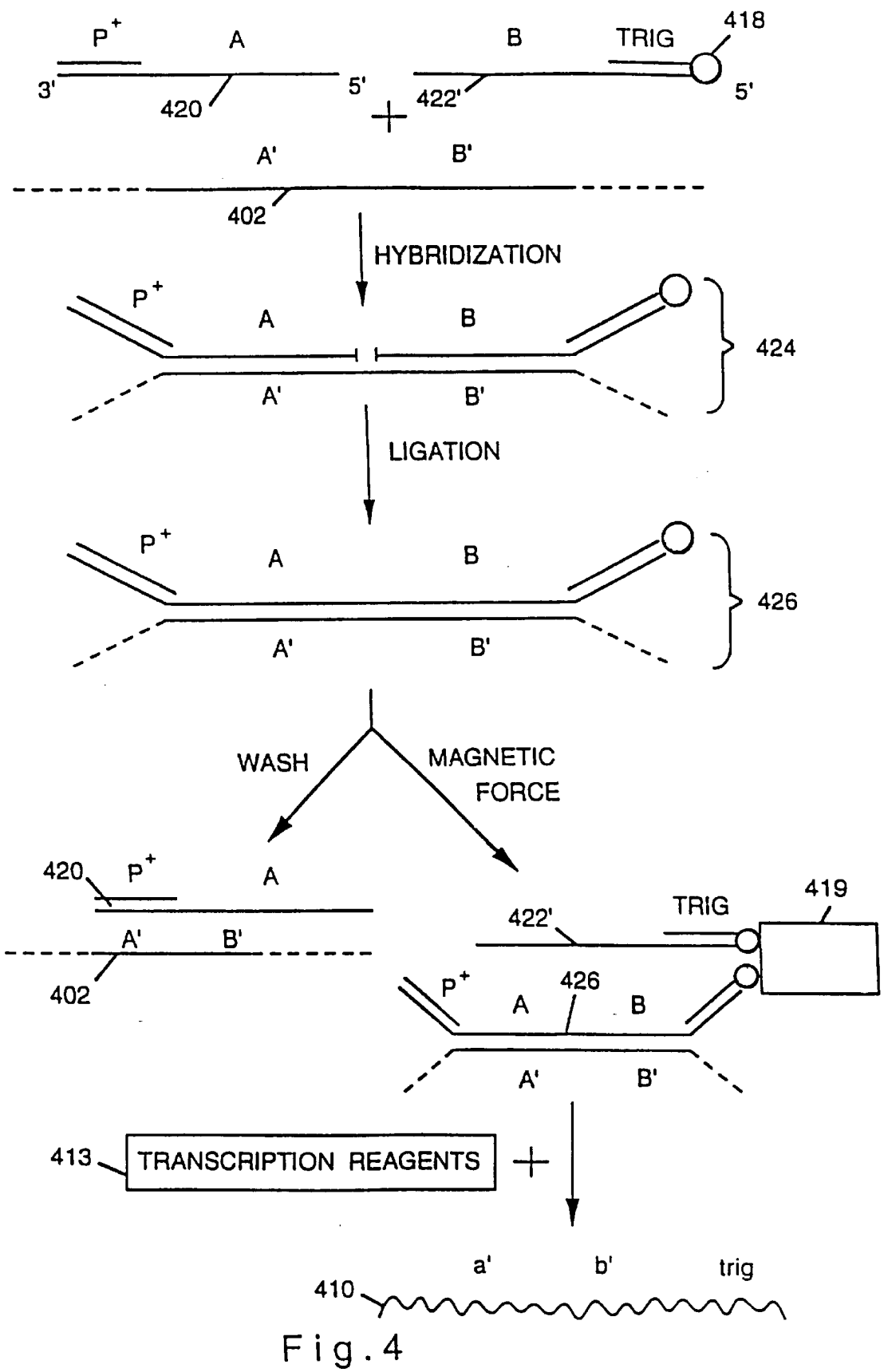
FIG. 4 shows a modification of the method in FIGS. 2 and 3 which eliminates the production of short RNA transcript having the sequence a' a which are transcribed from the first DNA molecules.

Reference is now made to FIG. 4 showing a modification in the method outlined in FIG. 2 and 3 which eliminates the production of short RNA transcript having the sequence a', which are transcribed from the first DNA molecule. First molecule 420 is identical to first molecule 220 in FIG. 2. Second molecule 422' is essentially identical to second molecule 222 in FIG. 2 and is linked to a magnetic bead 418 at its 5' terminal. Assayed DNA 402 is added to produce hybrid 424 optionally followed by ligating to yield ligation product 426. Magnetic force is then applied. All molecules linked to a magnetic bead, namely, free second DNA molecules 422 and ligation product 426, are drawn to the magnet 419, while molecules unlinked to magnetic beads, namely, first DNA molecules 420 and assay DNA molecules 402 are washed away. Transcription reagents 413 are added to the test vessel and since the only DNA molecules containing a promoter in the reaction mixture are ligation product 426, the only RNA transcripts which are produced are the triggering RNA molecules 410 containing the trig sequence. This modification enables detection of the presence of assayed DNA by the detection of mere amplification of RNA with no need to distinguish which type of RNA has been produced.

Figure 5:
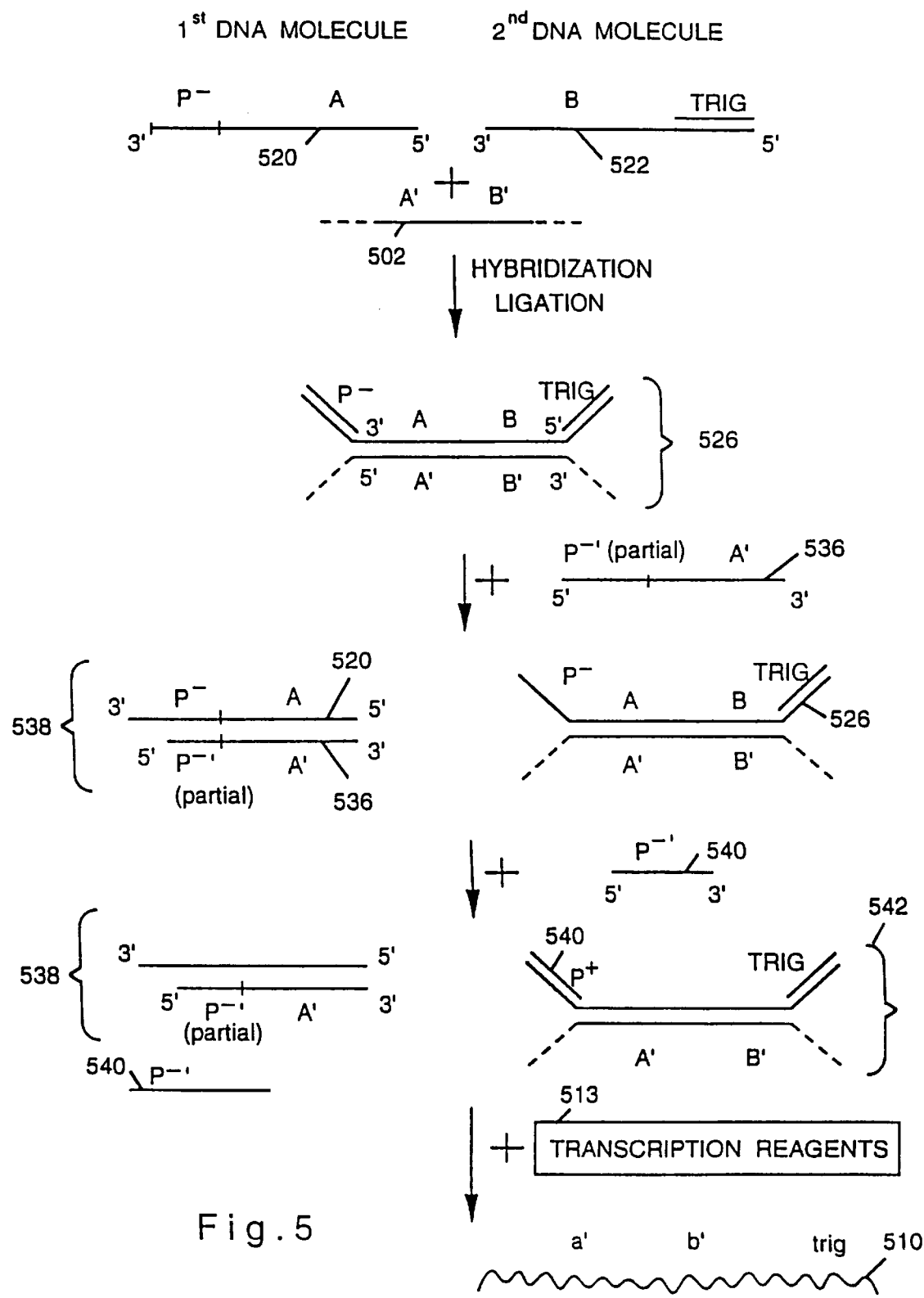
FIG. 5 shows another modification in the method outlined in FIGS. 2 and 3 also intended to eliminate production of contaminating short RNA transcripts having sequence a' transcribed from first DNA molecules.

Reference is now made to FIG. 5 which shows another modification in the method outlined in FIGS. 2 and 3 also intended to eliminate production of contaminating short RNA transcripts having sequence a' transcribed from first DNA molecules. First DNA molecule 520 contains only a single-stranded non-functional promoter ($P^-$). Assayed DNA 502 is added and allowed to hybridize with first 520 and second 522 DNA molecules and after addition of a ligase, ligation product 526 is obtained. To the reaction mixture a blocker molecule 536 is added containing at its 5' end a sequence which is partially complementary to part of the promoter sequence ($P^{-\prime}$ partial)) linked to a sequence A' complementary to sequence A or to a part thereof The blocker molecule 536 can hybridize only with free first molecules 520 to yield hybrid 538 and cannot bind to hybrid 526 since in this hybrid sequence A is already double-stranded. Since $P^{-\prime}$ is only partially complementary to the promoter, the presence of mismatches in hybrid 538 makes its promoter non-functional. At this stage, DNA molecules 540 containing a sequence $P^{-\prime}$ complementary to the full single-stranded promoter of the first DNA molecules are added. Molecules 540 can hybridize with hybrids 526 to give a hybridization product 542 having a functional double-stranded promoter. However, molecules 540 cannot hybridize with blocked hybrid 538, since the promoter of the hybrid is already partially double-stranded. By this modification free first molecules are blocked from forming a functional double-stranded promoter so that when transcription reagents 513 are added to the reaction mixture, no short RNA transcripts are produced and only RNA triggering molecules 510 are formed. The method outlined in this figure can be used in combination with the method of FIG. 2 in which case blocker molecule 540 contains also sequence A" of FIG. 2 and is used to increase the specificity of the method.

Figure 6:
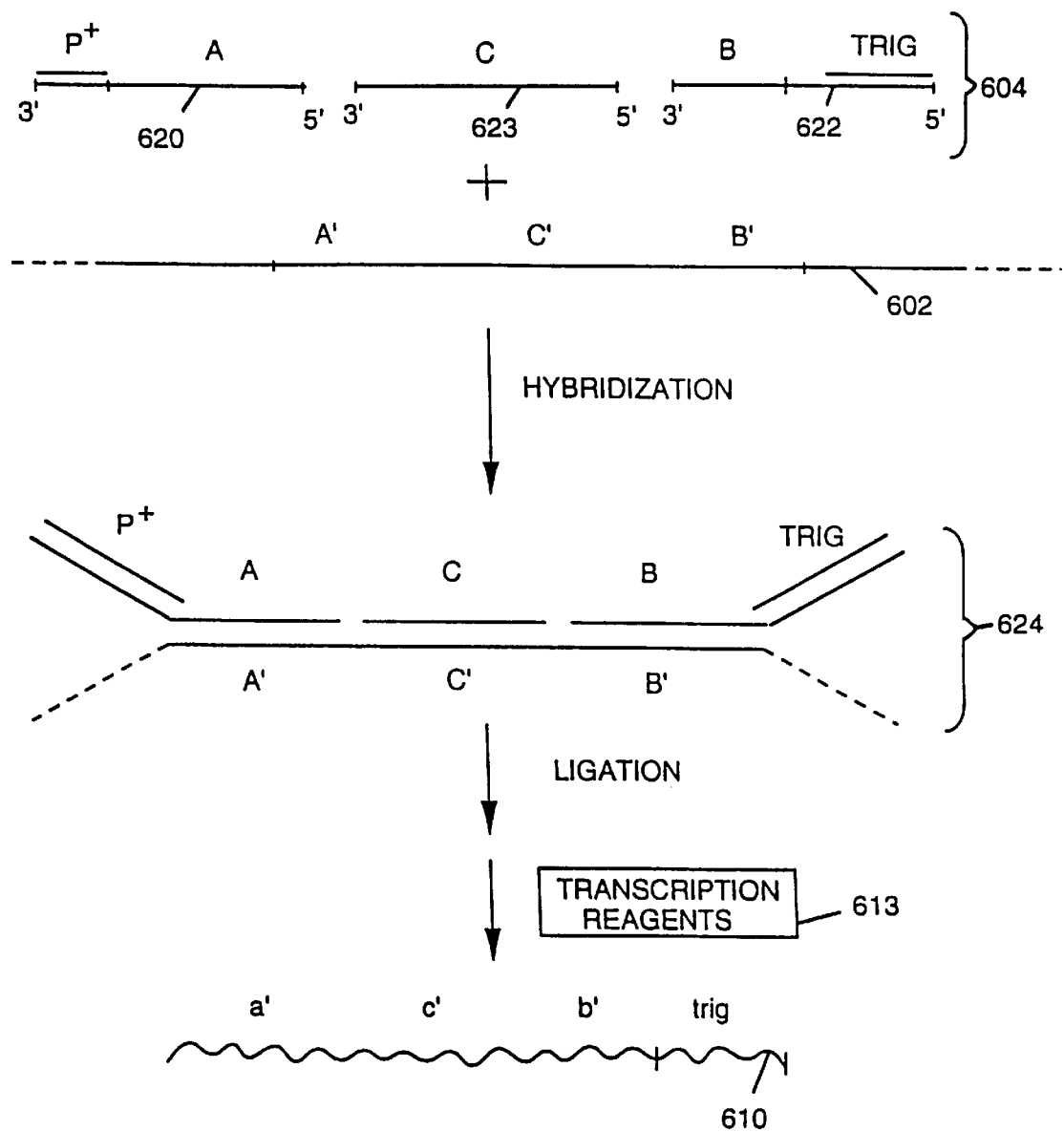
FIG. 6 shows a modification of the embodiment depicted in FIG. 1. In accordance with this embodiment, detection ensemble 604 comprises a first DNA molecules 620, a second DNA molecule 622 and a third DNA molecule 6223.

Reference is now made to FIG. 6 showing a modification of the embodiment depicted in FIG. 1. In accordance with this embodiment, detection ensemble 604 comprises a first DNA molecule 620, a second DNA molecule 622 and a third DNA molecule 623. These three molecules comprise single-stranded sequences A, B, C which are complementary to corresponding sequences A', B', C' in the assayed DNA sequence 602. Following hybridization, a hybridization product 624 is produced which is formed from the first, second and third DNA molecules on the one hand and the assayed DNA sequence on the other hand. Following an optional step of ligation and a step of addition of transcription reagents 613, a triggering RNA molecule 610 is produced in a manner similar to that described in FIG. 1.

RNA AMPLIFICATION ENSEMBLE

First embodiment of the invention

Figure 7:
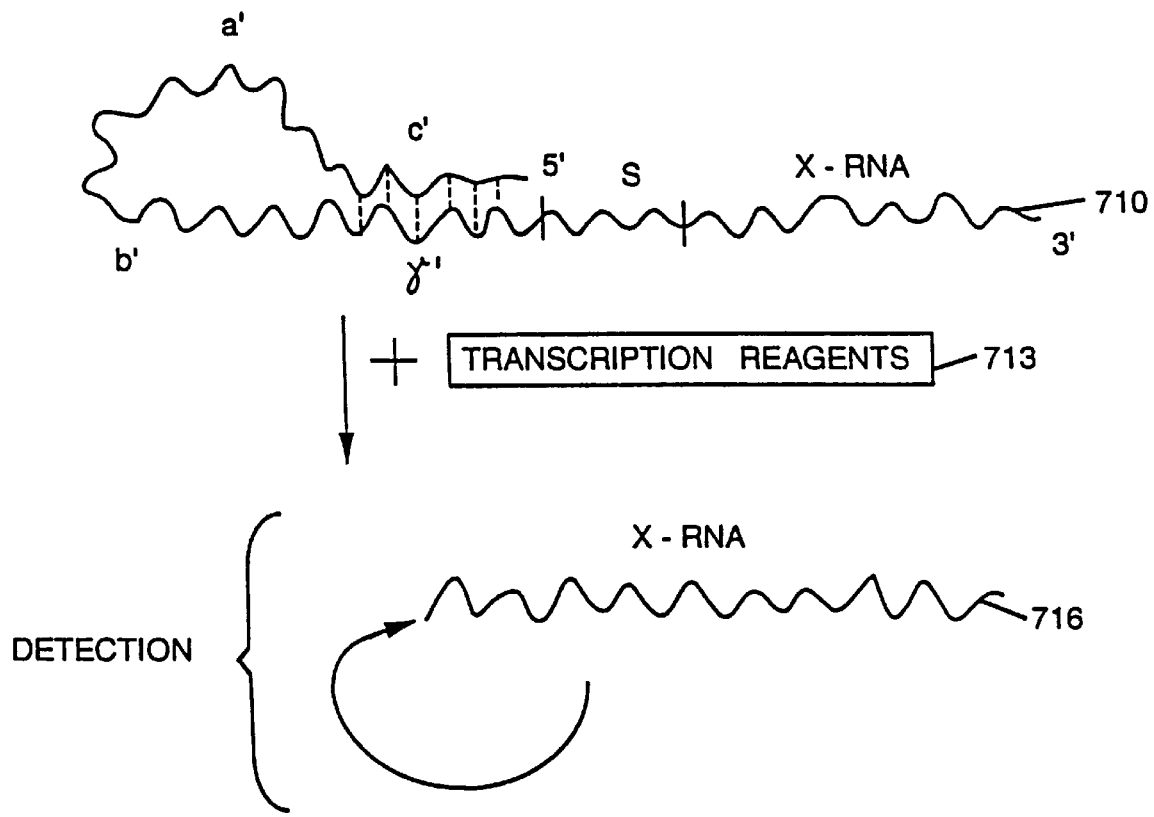
FIG. 7 shows an amplification ensemble in accordance with the first embodiment.

Reference is now made to FIG. 7 showing an RNA amplification ensemble according to a first embodiment of the invention. According to this embodiment, the triggering RNA molecule 710 which is a product of the detection ensemble contains a' and b' sequences transcribed from DNA sequence A and B. Upstream of sequence a' is sequence c' and downstream of sequence b' is sequence γ'. Sequence c' and γ' which are transcribed from sequences in the first and second DNA molecules, respectively, are orbitrary sequences complementary to each other. Downstream of sequence γ' is sequence s. Sequence s is a sequence that serves as a strong stop transcription sequence when molecule 710 is transcribed. Sequence s is linked to a self-replicating X-RNA sequence. The complementary sequences c'-γ' bring to the formation of a loop form which functions to minimize the interference of sequences a' and b' to the secondary structure of the X-RNA, which secondary structure is necessary for its self-replicating activity. In the presence of RNA transcription reagents 713, triggering RNA molecules 716 are produced, comprising an X-RNA sequence. The X-RNA sequence serves also as the signal molecule, the presence of which is detected by means known per se. Stop sequence s prevents the sequences a'and b' from being transcribed from molecule 710. Owing to its self-replicating property, large amounts of X-RNA molecules 716 are produced within a short period of time. The presence of large quantities of RNA will then serve as an indication for the presence of the assayed DNA in the sample.

Figure 8:
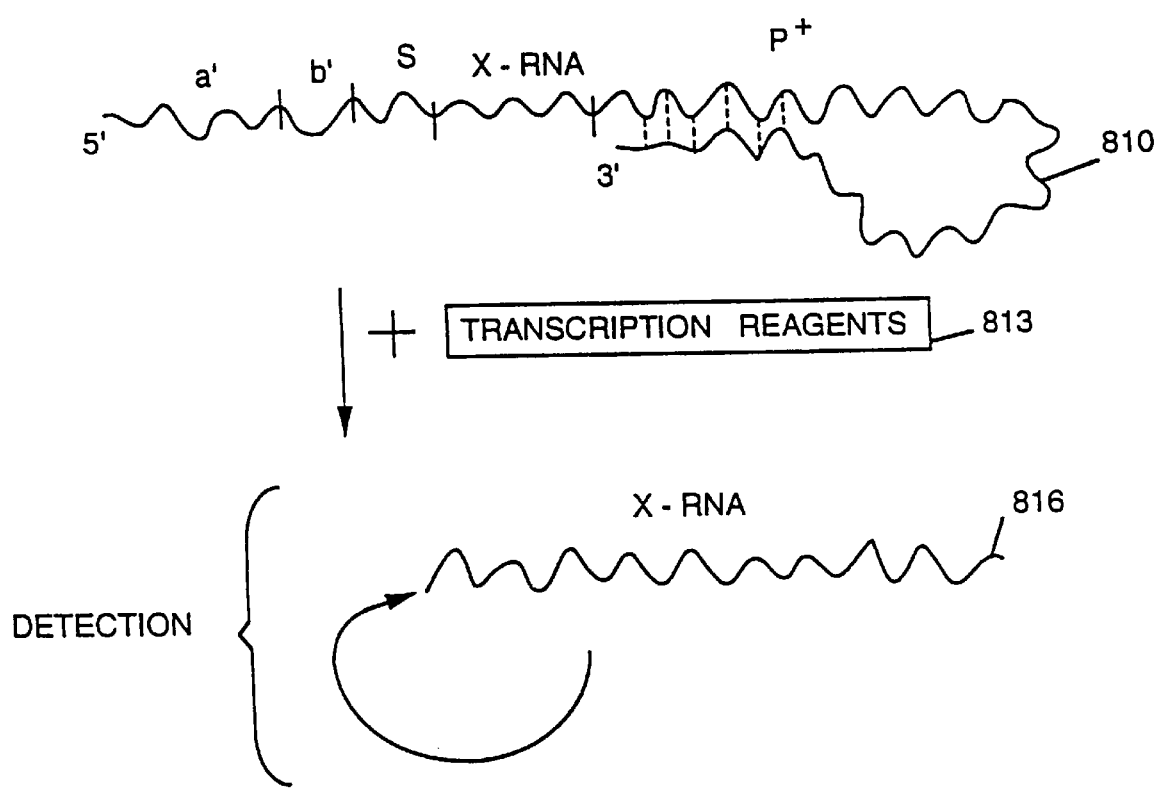
FIG. 8 shows a modification in the method of the first embodiment. According to this modification, the triggering RNA 810 comprises sequences a' and b' (transcribed from the assayed DNA) linked to sequence s which serves as a stop signal to the transcription as described above.

Reference is now made to FIG. 8 which shows a modification in the method of the first embodiment. According to this modification, the triggering RNA 810 comprises sequences a' and b' (transcribed from the assayed DNA) linked to sequence s which serves as a stop signal to the transcription as described above. Sequence s is linked to an X-RNA sequence which can serve as a template for the production of self-replicating X-RNA. This sequence is linked to a sequence capable of forming a hairpin loop so that the hybridized arms of this loop form a functional promoter $p^+$ in a manner similar to that previously reported for DNA (Kohli V. et a., Anal. Biochem., 208, 223–227, 1993). In the presence of a transcription reagents 813, this RNA promoter enables the production of self-replicating X-RNA 816, the detection of which signifies presence of the assayed DNA in the original sample.

Figure 9:
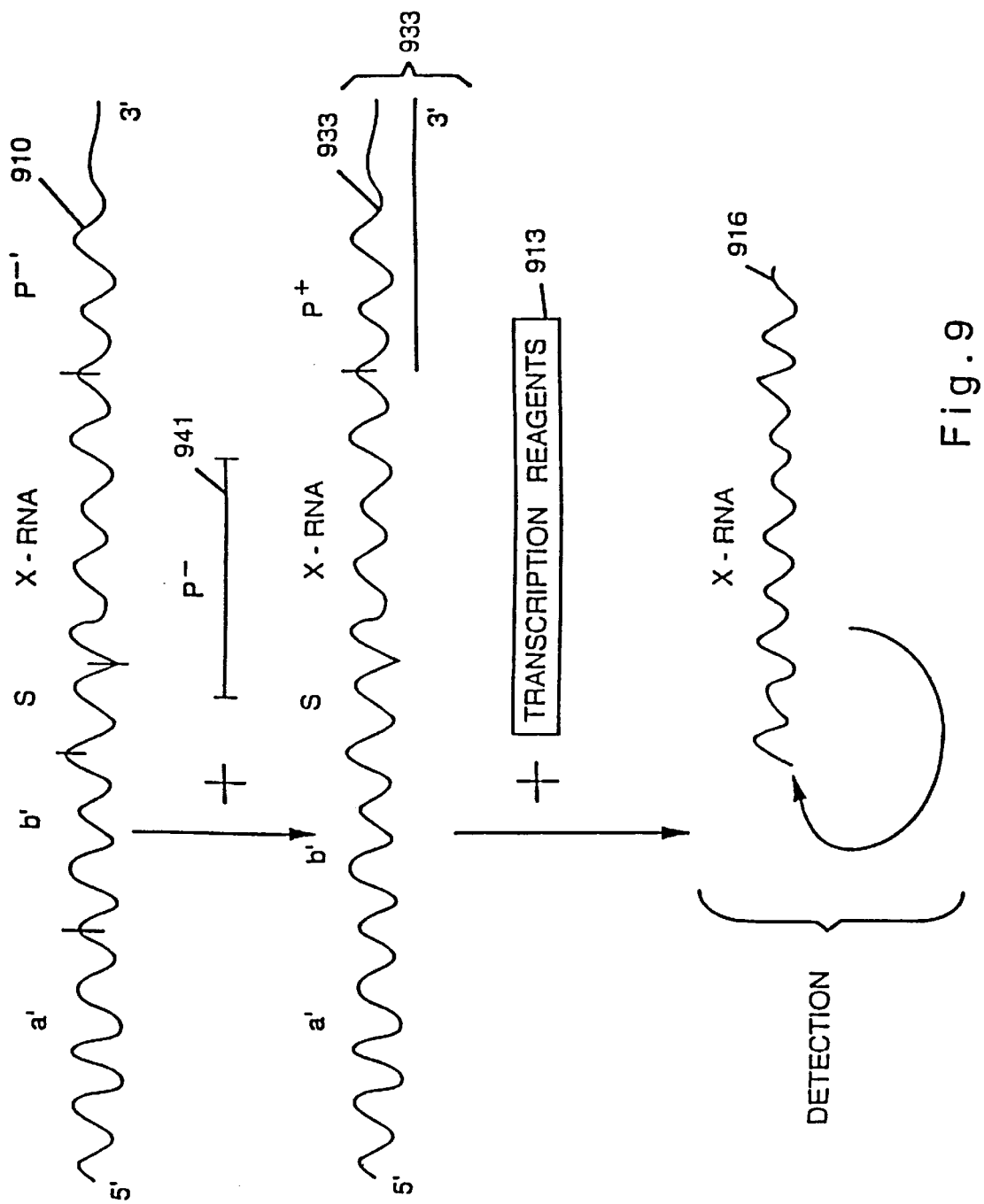
FIG. 9 shows another modification of the first embodiment. According to this modification triggering RNA molecule 910 comprises in addition to the a', b', s and X-RNA sequences (which were described with reference to FIG. 8) the template strand of a promoter sequence p_-.

FIG. 9 shows another modification of the first embodiment. According to this modification triggering RNA molecule 910 comprises in addition to the a', b', s and X-RNA sequences (which were described with reference to FIG. 8) the template strand of a promoter sequence $p^{-'}$. Optionally, DNA molecule 941, which comprises a sequence $P^-$ complementary to the single-stranded RNA promoter, is added and allowed to hybridize with molecule 910, to form DNA/RNA hybrid molecule 933 having a double-stranded RNA/DNA promoter and an RNA sequence which serves as a template. In the presence of transcription reagents 913, transcript 916 which is a self-replication X-RNA sequence, is produced.

Figure 10:
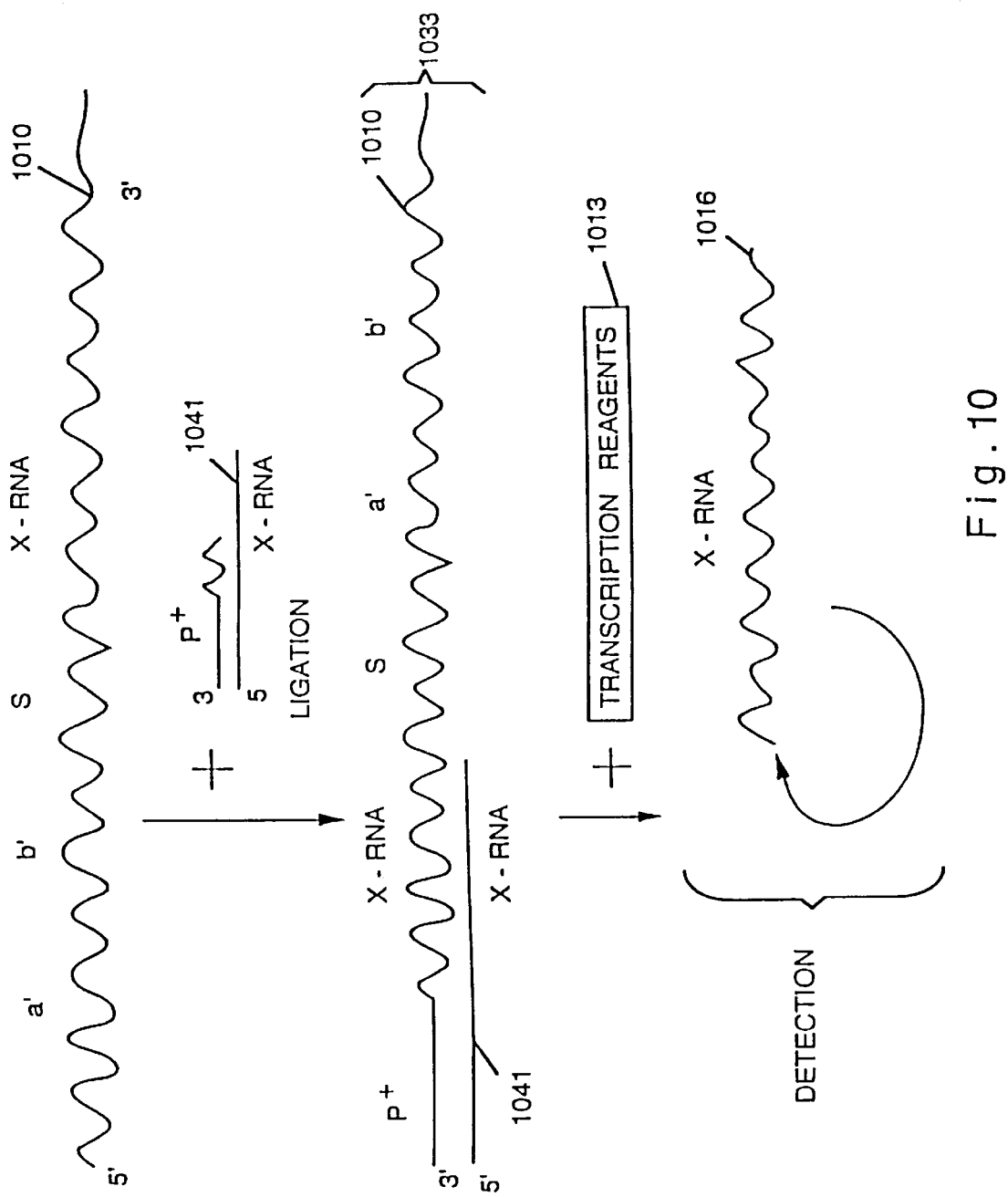
FIG. 10 shows a third modification of the first embodiment.

Reference is now made to FIG. 10 which shows a third modification of the first embodiment. Triggering RNA 1010 comprises sequences, a', b', s and X-RNA as described above. A DNA molecule 1041 is added which comprises a double-stranded functional DNA promoter of which the non-template strand is linked to a DNA sequence complementary to all or to part of the X-RNA sequence of molecule 1010. The last nucleotide or several nucleotides of the template strand of molecule 1041 is optionally an RNA nucleotide. Molecules 1010 and 1041 are allowed to hybridize, and following ligation of the last RNA or DNA nucleotide of molecule 1041 and the first nucleotide of hybrid 1010, hybrid 1033 is formed. In the presence of transcription reagents 1013 self-replicating RNA 1016 is produced.

Second embodiment of the invention

Figure 11:
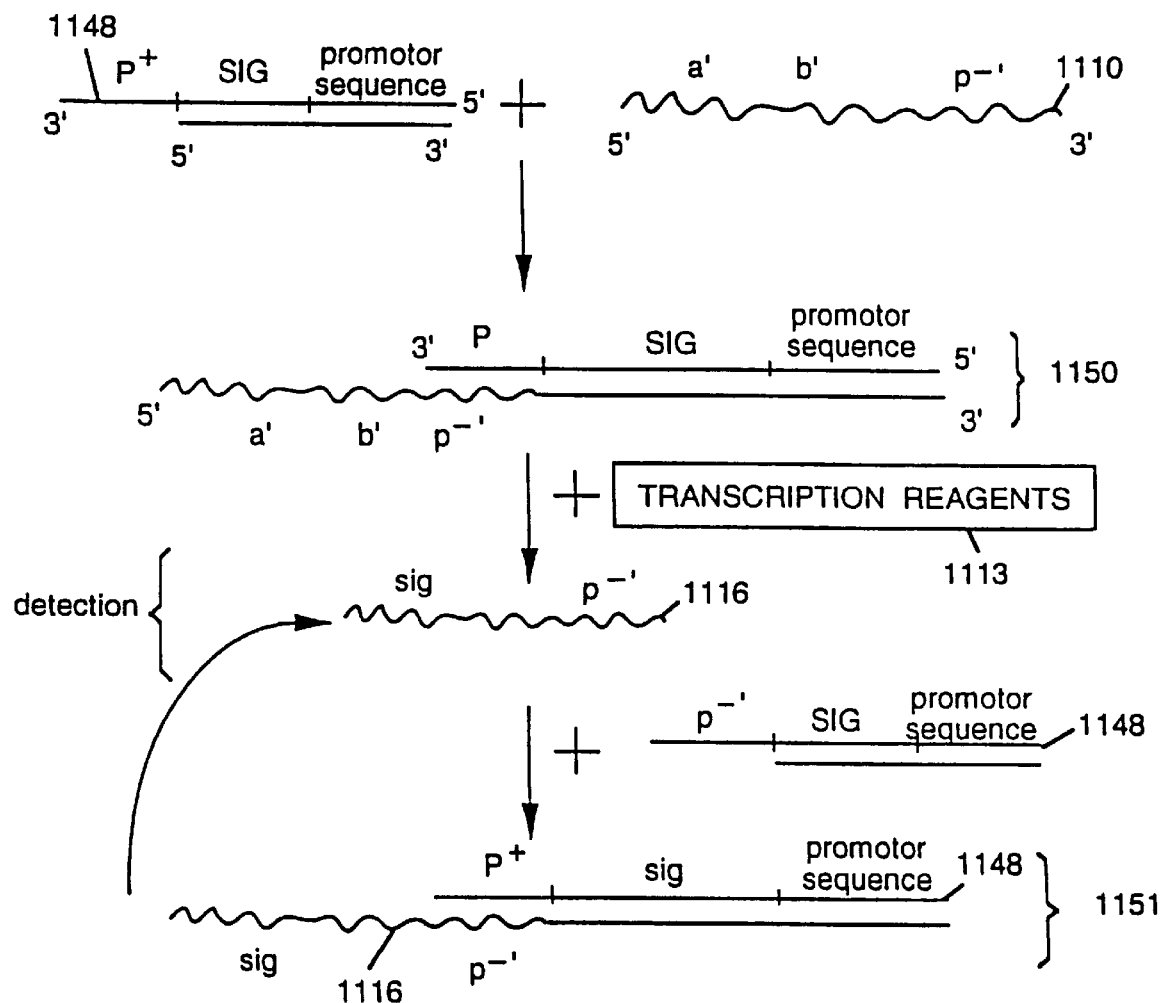
FIG. 11 shows an amplification ensemble in accordance with the second embodiment.

Reference is now made to FIG. 11 showing an RNA amplification ensemble according to the second embodiment of the invention. According to this embodiment, the triggering RNA molecule 1110 product of the detection ensemble, contains sequences a' and b' linked to the triggering sequence $p^{-'}$ which is a single-stranded sequence complementary to an essential part of the single-stranded promoter $P^-$ of a fourth DNA molecule 1148. Fourth DNA molecule 1148 contains at the 3' end of its template strand a single-stranded promoter sequence $P^{-'}$, linked to a double-stranded signal DNA sequence SIG, which is in turn linked to a DNA sequence capable of being transcribed to the triggering sequence p-' termed "promoter-sequence" in the figure. In some cases $P^-$ of molecule 1148 may be partially double-stranded and is only single-stranded in a part essential for the promoter's function. When RNA molecule 1110 is added to molecule 1148, the triggering sequence $p^{-'}$ of molecule 1110 hybridizes with sequence $P^{-'}$ of molecule 1148 to form an RNA/DNA heteroduplex 1150 having a double-stranded functional promoter $P^{+'}$ consisting of one DNA strand and one RNA strand or partial RNA strand. Upon addition of transcription reagents 1113, RNA transcript 1116, which is the signal RNA molecule comprising the RNA signal sequence "sig" and sequence $p^{-'}$, is produced. RNA transcript 1116 can in turn hybridize with the fourth DNA molecules 1148 to produce RNA/DNA heteroduplexes 1151 which in the presence of the transcription reagents 1113 causes production of more RNA transcripts 1116 in a self-amplifying manner. Thus, the amounts of signal RNA molecules in the medium increases rapidly and in a short period of time large quantities are produced. The signal molecule can then be detected by means known per se, either by detecting of the presence of the specific signal sequence or by merely determining the quantity of RNA in a sample, for example, by change in light absorbance. The presence of the signal RNA molecule indicates the existence of the assayed DNA in the original sample.

Third embodiment of the invention

Figure 12:
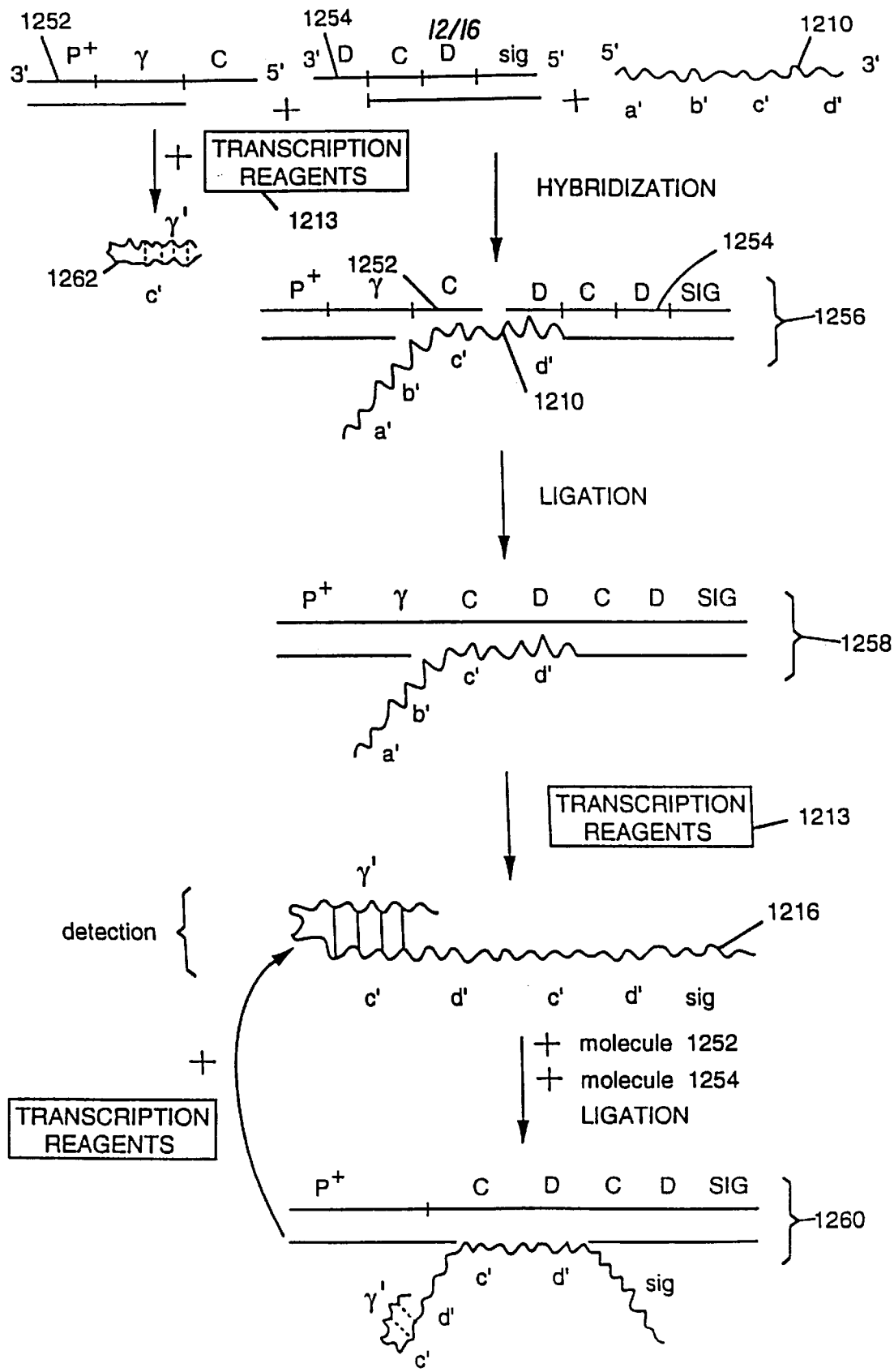
FIG. 12 shows an amplification ensemble in accordance with the third embodiment.

Reference is now being made to FIG. 12 which shows an RNA amplification ensemble according to the third embodiment of the invention. The RNA triggering molecule 1210, product of the detection ensemble, comprises sequences a' and b' linked to sequences c'and d' which are complementary to the single-stranded sequences C and D in the fifth 1252 and sixth 1254 DNA molecules, respectively. Fifth DNA molecule 1252 comprises a double-stranded functional promoter $P^{+'}$ linked to a double-stranded sequence γ linked to a single-stranded sequence C. Sequence γ and sequence C are complementary to each other. Sixth DNA molecule 1254 comprises at the 3' end of the template strand a single-stranded sequence D, linked to double-stranded sequences, C, D and a signal DNA sequence.

The two DNA molecules 1252 and 1254 are allowed to hybridize with RNA transcript 1210 to give an RNA/DNA heteroduplex 1256. In this hybridization product molecules 1252 and 1254 are joined together by RNA transcript 1210. A ligase is added to ligate the adjacent ends of DNA molecules 1252 and 1254 to yield a ligation product 1258. In the presence of transcription reagents 1213, an RNA molecule 1216 is produced. In this molecule sequence γ' and c' which are complementary, form a loop. The signal sequence sig in molecule 1216 can then be detected by means known per se. In addition, RNA molecule 1216 can be further made to hybridize with more fifth 1252 and sixth 1254 DNA molecules to form an RNA/DNA heteroduplex 1260 optionally followed by ligation. In the presence of the transcription reagents 1213 more RNA transcripts 1216 are transcribed from hybrid 1260 which in turn cause formations of more heteroduplexed 1260, and the reaction can continue in a self-amplifying manner.

In the presence of a transcription system 1213, fifth DNA molecules 1252, which comprises a functional promoter produces short RNA transcripts 1262. These short RNA transcripts however cannot interfere with the hybridization of the fifth DNA molecules 1252 with the triggering RNA 1210 or with RNA transcript 1216, wince due to the presence of complementary sequences c' and γ' a loop is formed.

Figure 13:
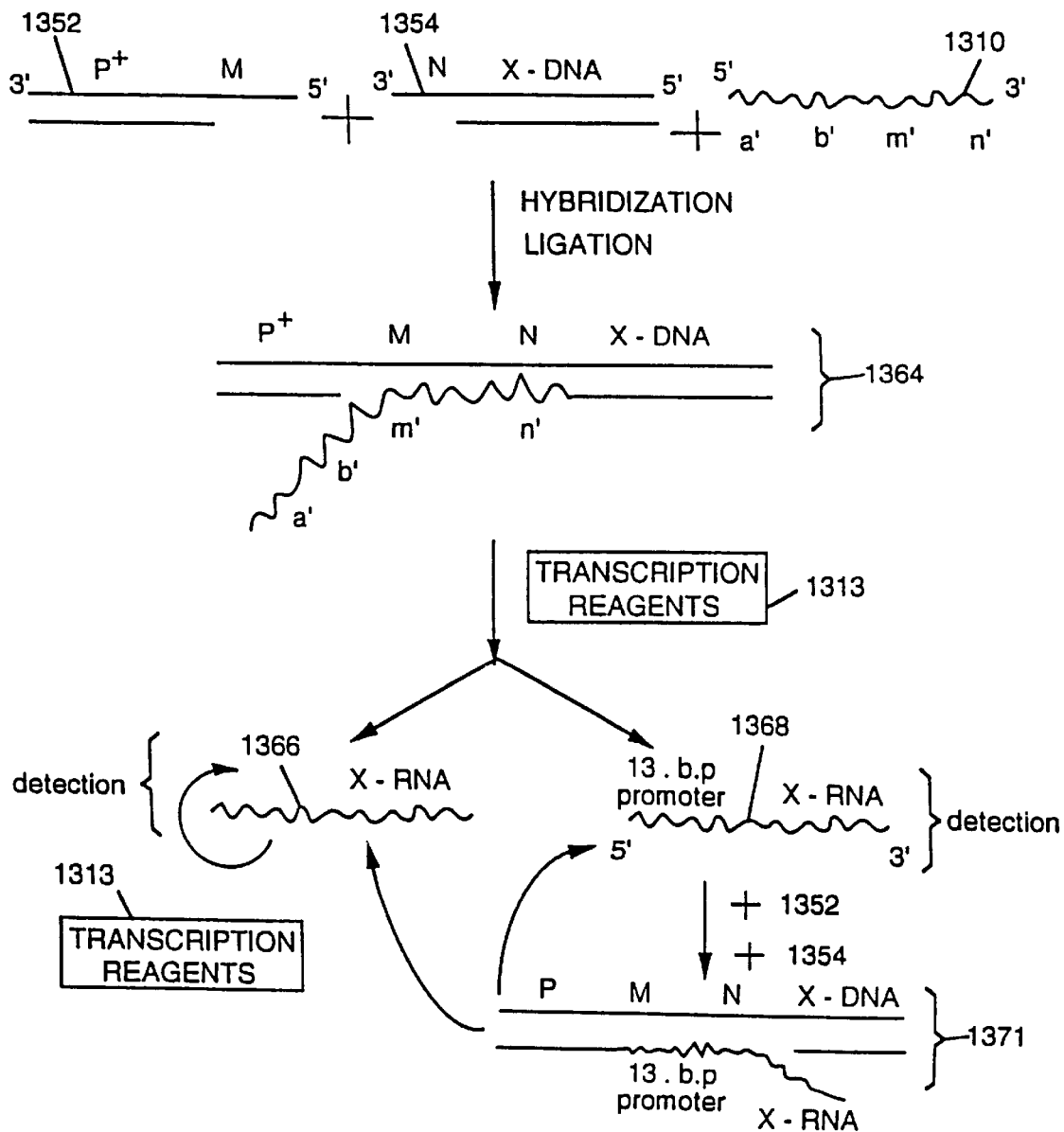
FIG. 13 shows a modification of the embodiment of FIG. 12.

Reference is now being made to FIG. 13 which shows a modification of the third embodiment of the invention. Fifth molecule 1352 comprises a functional double-stranded promoter P$^+$ and a short single-stranded 5' end of sequence M. The single-stranded sequence M may be a 5' end nonessential part of the promoter or a short linker sequence. Sixth molecule 1354 is a DNA molecule comprising an X-DNA sequence coding for a self-replicating X-RNA, which molecule is single-stranded in a small region at the 3' end of the template strand having a sequence N. According to this modification the RNA transcript 1310, the product of the detection ensemble, comprises the a'and b' sequences attached to a single-stranded sequence m' which is complementary to the small single-stranded region M in fifth molecule 1352, joined to a single-stranded sequence n' which is complementary to the single-stranded sequence N in sixth molecule 1354. RNA transcript 1310 hybridizes with DNA molecules 1352 and 1354,and optionally with the aid of a ligase, joins the two DNA molecules to form an RNA/DNA heteroduplex 1364.

In the presence of transcription reagents 1313 heteroduplex 1364 is transcribed to two products: an X-RNA transcript 1366 which is self-replicating in the presence of a transcription system 1313; and a transcript 1368 having as its 5' end a sequence complementary to 13 base pairs of a promoter linked to an X-RNA sequence 1366 which is self-replicating. RNA transcript 1368 can join additional fifth and sixth DNA molecules to form RNA/DNA heteroduplex 1371 which heteroduplex in the presence of a transcription system can give rise again to X-RNA molecules 1366 and transcripts 1368. The detection is then performed in a manner similar to the above.

Fourth embodiment of the invention

Figure 14:
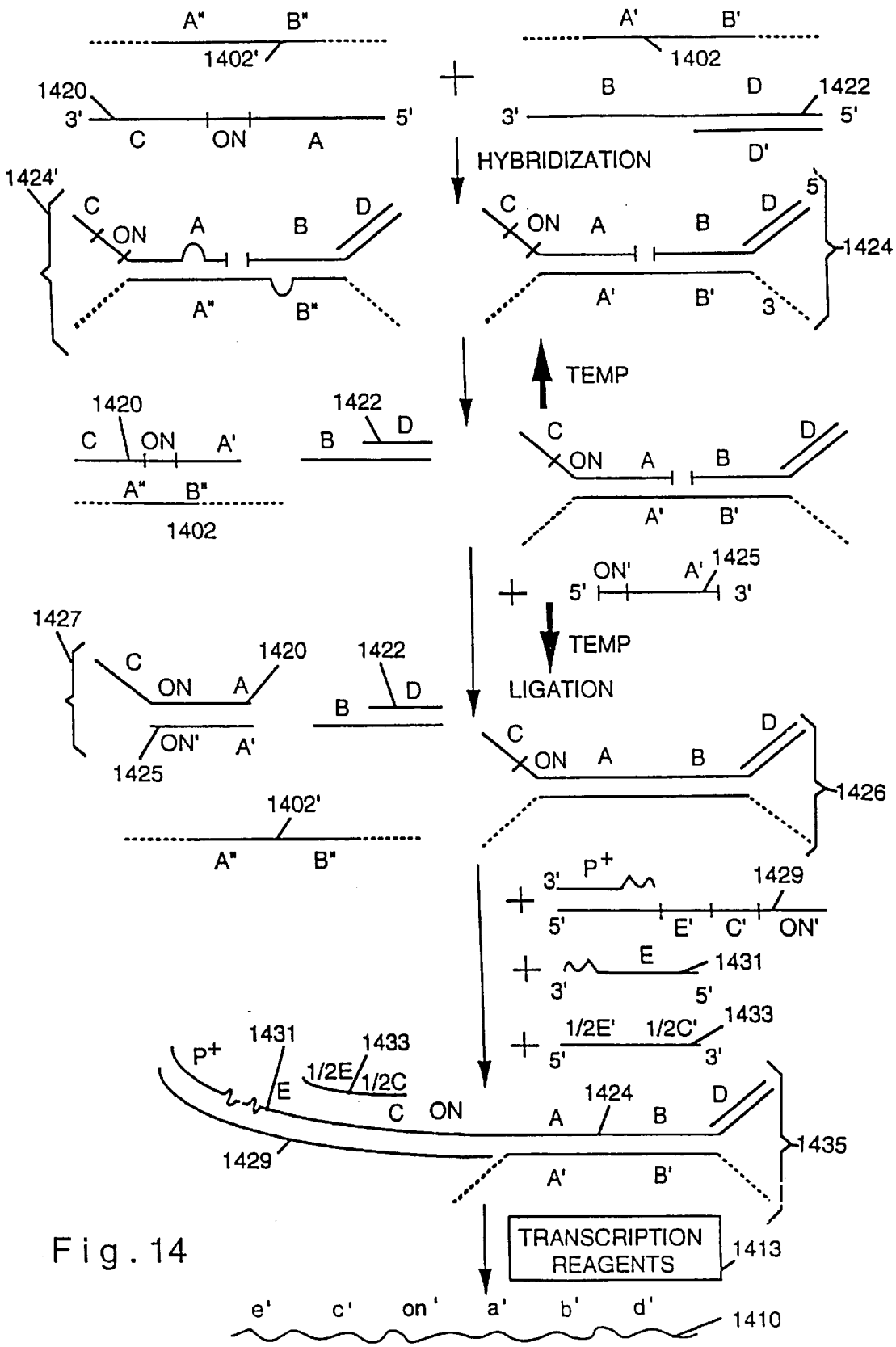
FIG. 14 shows a detection ensemble in accordance with the fourth embodiment.
Figure 15:
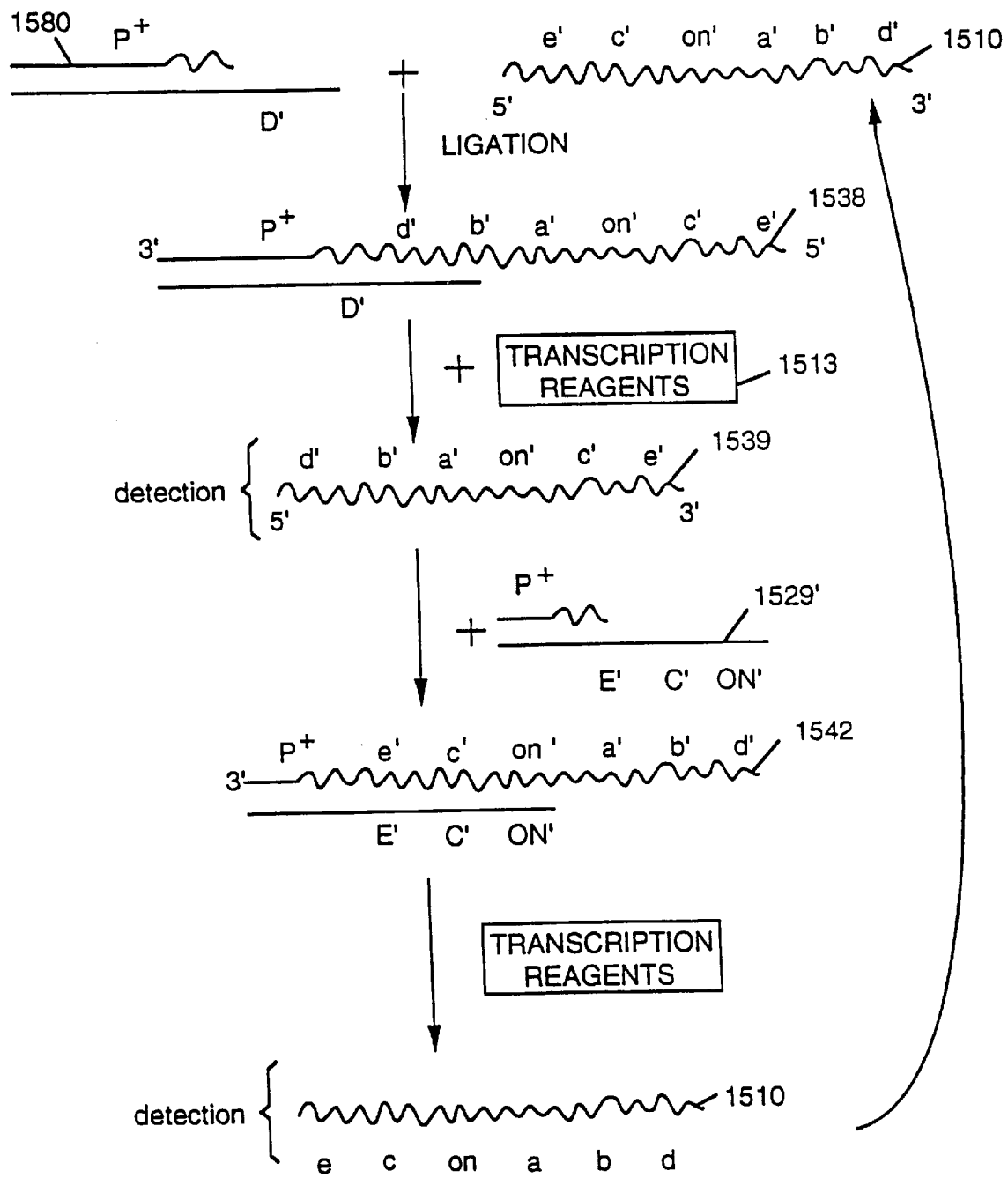
FIG. 15 shows an amplification ensemble in accordance with the fourth embodiment.

The fourth embodiment of the invention is shown in FIGS. 14 and 15. The first, second and third embodiments described above, make use of the same detection ensemble and differ from one another in the amplification ensemble. Against this, the fourth embodiment differs from the others in both the detection as well as the amplification ensembles.

The detection ensemble in accordance with this embodiment is shown in FIG. 14. First DNA molecule 1420, which in this embodiment is completely single-stranded, comprises at its 3' end an arbitrary sequence C, linked to a short sequence of 1 to 5 bases termed ON and linked to a sequence A. Second DNA molecule 1422 comprises at its 3' end a sequence B linked to an arbitrary double-stranded sequence D–D'.

Sequence A of the first molecule is complementary to sequence A' in the 5' end portion of the assayed DNA and sequence B of the second DNA molecule is complementary to the sequence B' in the remaining 3' end portion of the assayed DNA 1402.

At times, the sample contains also a sequence 1402' comprising sequences A" and B" which are not fully complementary to sequences A and B in first and second molecules 1420 and 1422, respectively. This may be so, for example, in the case of genetic polymorphism. The molecules in the mixture are allowed to hybridize, producing perfect hybridization products 1424 and imperfect hybridization products 1424'.

In a similar manner as in the embodiment described in FIG. 3, conditions are provided so that essentially only imperfect hybrids 1424' are melted. A blocker molecule 1425 is added to the mixture which during cooling hybridizes to free first DNA molecules 1420. The free first DNA molecules include both first DNA molecules present a priori in the sample and first DNA molecules which were freed from hybrid 1424' after melting. Molecule 1425 comprises sequences ON' and A' complementary to sequence ON and A, respectively, in molecule 1420 and consequently hybrid 1427 is produced. In order to ensure that all free. DNA molecules will be blocked by blocker molecules 1525, an excess of the blocker molecules is added.

To the sample are now added molecule 1429, 1431 and 1433 which together are able to form a functional promoter with the ligation product of hybrid 1424 which is 1426 while they are not able to form a functional promoter with hybrid 1427, thus avoiding the production of short RNA transcripts having the sequence c—on—a.

Molecule 1429, termed herein "promoter molecule", comprises a double-stranded promoter P$^+$. One or a few of the RNA nucleotides at the 5' end of the template strand of the promoter are optionally RNA nucleotides. This molecule can be produced by a nucleic acid synthesizer. The non-template strand of the promoter is linked to sequence E', C' and ON'.

Molecule 1431 termed herein "adapter molecule" comprises a single-stranded DNA sequence optionally having one or a few RNA nucleotides at its 3' end. The purpose of the adapter molecule is to provide a standard sequence having an initial RNA nucleotide which can bind to the RNA nucleotide of the promoter at its one end and to the first DNA molecule (with the aid of a joiner molecule) on its other end, in a case where an RNA molecule is required on the 3' end. When an RNA molecule is not required, the adapter molecule provides a standard sequence common to all reactions. Alternatively, the sequence contained in the adapter molecule may be added to each first DNA molecule when synthesized so that the need for a separate molecule is eliminated.

Molecule 1433 termed herein "joiner molecule", it comprises. at its 5' end a part (e.g. a half) of E' and at its 3' end a part (e.g. a half) of C'. This molecule serves to join adapter molecule 1431 and first DNA molecule 1420. In addition, hybridization with this molecule renders the ON sequence essential for hybridization of the promoter molecule 1429 to first DNA molecule 1420. The fact that the ON sequence becomes essential avoids binding of promoter molecule 1429 to blocked hybrid 1427 in which the ON sequence is covered, and thus the production of short contaminating sequences is avoided.

When the molecules are added to hybrid 1424, joiner molecule 1433 joins the 3' end of molecule 1420 (in the C sequence) and the 5' end of adapter molecule 1431 (in the E sequence). After this joining, the promoter molecule 1429 can hybridize to sequence E of the adapter molecule 1431 and sequences C and ON in first molecule 1420. A ligase then ligates the adjacent ends of the RNA nucleotides both in promoter molecules 1429 and adapter molecule 1131 (when present) resulting in hybrid 1435. Adjacent RNA nucleotides can be ligated by the T$_4$ DNA which is known to be able to ligate between RNA Nucleotides (Moore et al., *Science*, 256, 992–997, (1992). Ligation that occurs when the 3' molecule is comprised of RNA and the 5' molecule is comprises of DNA and also efficiently ligated by T$_4$ DNA ligate (Nath and Hurwitz, *J. Biol. Chem.*, 249, 3680–3688 (1974).

Promoter molecules 1429, together with the remaining components cannot bind to blocked hybrid 1427 since in this hybrid the sequence ON is blocked, which blockage prevents hybridization.

In the presence of transcription system 1413, RNA transcript 1410 is produced.

The amplification ensemble is shown in FIG. 15. The ensemble compromises promoter molecule 1529', being the same as molecule 1429 in FIG. 14, and an opposite promoter molecule 1580 that is a promoter which is a double-stranded promoter linked to a sequence D', complementary to sequence d' in the transcript 1510. Transcript 1510 being identical to 1410 in FIG. 14 hybridizes to D' sequence of opposite promoter 1580 and with the aid of a ligase an RNA/DNA hybrid 1538 is formed. In the presence of a transcription system 1513, a new RNA transcript 1539 is transcribed. The template of this transcript is the RNA sequence of hybrid molecule 1538. It is known that RNA can serve as a transcript for RNA production (Leary S. L. et al., Gene, 106, 93–6 (1991). Transcript 1539 can hybridize with promoter molecule 1529' to give hybrid 1542. The product of hybrid 1542 is again molecule 1510 which can activate opposite promoter 1580 and so on. In this embodiment the transcription product of each hybrid 1538 or 1542 activates the reciprocal promoter in a "ping pong" manner.

Figure 16:
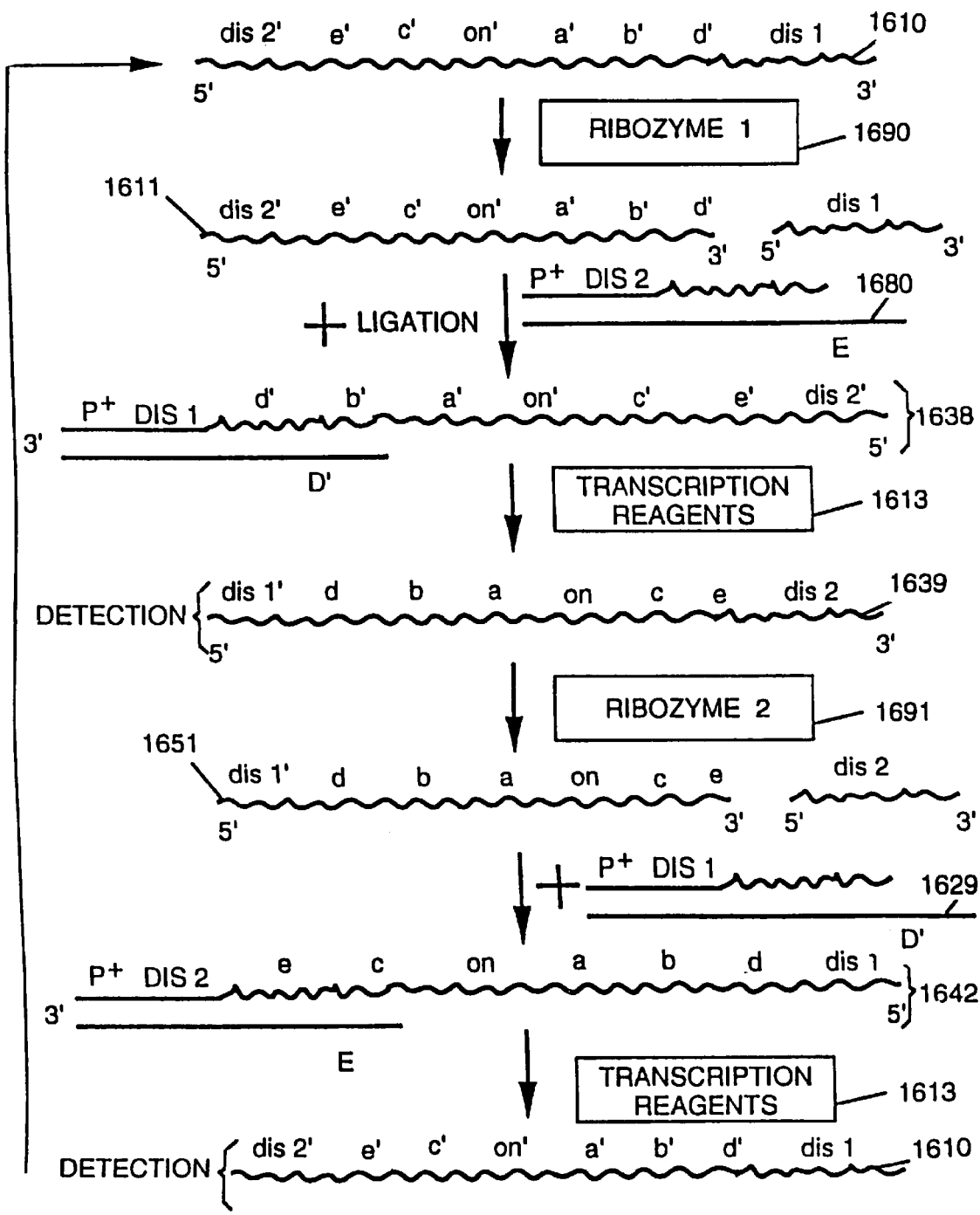
FIG. 16 shows a modification of the embodiment of FIG. 15.

The modification of the amplification ensemble of the fourth embodiment is now shown in FIG. 16, with all identical elements to those of the original amplification ensemble shown in FIG. 15 having the same last two digits.

RNA transcript 1610 product of the detection ensemble comprises in the 5'→3' direction the following sequences: one variant of the dis sequence - a dis2' sequence which is transcribed from one variant of the DNA initiation sequence; e', c', on', a', b', d' which are the same as explained in FIGS. 14 and 15; and dis sequence which is another variant of the dis sequence.

To the reaction mixture is added one type of rybozyme 1690 termed "rybozyme1" which is able to specifically cut the dis1 sequence from the 3' end of molecule 1610 to give truncated RNA molecule 1611. RNA molecule 1611 reacts with opposite promoter 1680, which comprises a double-stranded promoter, the coding strand of which is attached to sequence DIS1, and optionally with the aid of a ligase, gives hybrid 1638. In the presence of transcription reagent 1613 RNA transcript 1639 is produced, which may be detected.

A second type of rybozyme 1591 termed "rybozyme2" which is able to cut the dis2 sequence of transcript 1639 is used to give truncated RNA molecule 1651.

RNA molecule 1651 reacts with promoter molecule 1629, which contains a double-stranded promoter, the coding strand of which is attached to sequence DIS2, and optionally with the aid of a ligase gives hybrid 1642. In the presence of transcription reagents 1613 RNA transcript 1610 is produced again and the whole amplification cycle can restart.

I claim:

1. A method for detecting the presence of an assayed nucleic acid sequence in a sample, comprising the steps of:
   (a) reacting the sample with a detection ensemble comprising:
      a first DNA molecule having a promoter sequence at the 3' end and a 5' end sequence which is complementary to the 5' end portion of the assayed nucleic acid sequence;
      a second DNA molecule comprising a single-stranded 3' end sequence being complementary to a 3' end portion of the assayed nucleic acid sequence, and further comprising a sequence, at the 5' end which can be transcribed into a triggering RNA sequence capable of initiating a reaction in an appropriate transcription system in which an RNA molecule having a signal RNA sequence is being produced; wherein the 3' end sequence of the second DNA molecule and the 5' end sequence of the first DNA are complementary to at least part of said assayed nucleic acid sequence leaving an intermediary portion in the assayed nucleic acid having no complementary counterpart in either the first or the second DNA molecules, in which case the detection ensemble further comprises
      a third DNA sequence being complementary to said intermediate portion;
   (b) incubating under conditions to allow hybridization of said first DNA molecule and said second DNA molecule and were present also said third DNA molecule with said assayed nucleic acid sequence, and optionally adding a ligase to allow ligation of adjacent ends of said first, second and third DNA molecules;
   (c) adding transcription reagents comprising a DNA dependent-RNA polymerase and RNA nucleotides and incubating under conditions to allow the formation of RNA transcripts having said triggering RNA sequence;
   (d) contacting the RNA transcripts with an RNA amplification ensemble, a priori, lacking the triggering RNA, in which a triggering RNA sequence induces formation of RNA molecules containing the signal RNA sequence; and
   (e) detecting the presence of said signal RNA sequence, positive results indicating the presence of said assayed nucleic acid sequence in said sample.

2. A method according to claim 1, wherein after step (b) the temperature is transiently raised to a point in which only essentially perfectly matched hybrids formed in step (b) remain hybridized while all other hybrids in which the individual strands do not perfectly match to one another are melted.

3. A method according to claim 2, wherein after raising the temperature, blocker DNA or RNA are added which are complementary to a sequence in said first or said second DNA molecule, whereby said blocker molecules compete with the assayed DNA sequence in hybridization to the first or the second DNA molecule, and consequently rehybridization of assayed DNA sequences which are not essentially perfectly complementary to the molecules of said detection ensemble is avoided.

4. The method according to claim 1, wherein said promotor sequence is double-stranded in its essential parts and hence functional.

5. The method according to claim 1, wherein said promotor sequence is single-stranded in at least an essential part thereof and during or after step (b) a sequence which is complementary to the single-stranded part of the promoter is added, rendering the promoter functional.

6. The method according to claim 5, wherein prior to addition of the sequence complementary to the single-stranded part of the promoter sequence, blocker DNA or RNA molecules are added which hybridize to free first DNA molecules in a manner so as to avoid subsequent hybridization of the sequences complementary to the single-stranded part of the promoter to said free first DNA molecule, said blocker molecule being incapable of hybridizing to said first DNA molecules which have already hybridized to said assayed DNA sequence.

7. A method according to claim 1, wherein said second DNA molecules are bound to a solid support and following step (b) there is a washing step intended for removal of DNA molecules which are unbound to the solid support.

8. The method according to claim 1, wherein:
said RNA amplification ensemble comprises: a fourth DNA molecule comprising a promoter which is single-stranded in at least an essential part thereof and is thus inactive, and further comprises a signal DNA sequence;
said triggering RNA sequence being complementary to said single-stranded part of the promoter of the fourth DNA molecule and upon hybridization thereof to the single-stranded part of the promoter, the promoter becomes functional and in the presence of the transcription reagents, an RNA transcript is transcribed comprising a sequence transcribed from the DNA signal sequence.

9. A method for detecting the presence of an assayed nucleic acid sequence in a sample, comprising the steps of:
(a) reacting the sample with a detection ensemble comprising:
a single-stranded DNA molecule having from its 3' to its 5' end three sequence portions linked to one another comprising a first arbitrary portion, a second arbitrary portion of 1–5 bases long, and a 5' end sequence which is complementary to the 5' end portion of the assayed nucleic acid sequence;
a second DNA molecule comprising a single-stranded 3' end sequence being complementary to a 3' end portion of the assayed nucleic acid sequence, and further comprising a third arbitrary portion which third arbitrary portion is double-stranded;
(b) incubating under conditions to allow hybridization of the assayed nucleic acid sequence to said single-stranded DNA molecule and to said second DNA molecule to produce DNA hybrids;
(c) raising the temperature to a point in which only essentially perfectly matched hybrids formed in step (b) remain hybridized while all other hybrids in which the individual strands do not perfectly match to one another are melted;
(d) adding a blocker DNA molecule, being a single-stranded DNA molecule comprising at its 5' end a sequence complementary to said second arbitrary portion and a sequence, at its 3' end complementary to the 5' end portion to the assayed DNA, providing conditions allowing hybridization of said blocker molecule with fee said single-stranded DNA molecule;
(e) adding a promoter DNA molecule, comprising a double-stranded functional promoter and a sequence complementary to the first and second arbitrary portions attached to the non-template strand of the promoter, and providing conditions for hybridization, whereby a hybrid comprising the assayed DNA sequence, said promoter DNA molecule, said single-stranded DNA and said second DNA molecule is obtained from which an RNA transcript can be transcribed;
(f) adding transcription reagents comprising a DNA-dependent RNA polymerase and RNA nucleotides and incubating under conditions to allow the formation of RNA transcripts having a triggering RNA sequence capable of initiating a reaction in an appropriate transcription system in which an RNA molecule having a signal RNA sequence is being produced;
(g) contacting the RNA transcripts with an RNA amplification ensemble in which the triggering RNA sequence induces formation of RNA molecules containing the signal RNA sequence; and (h) detecting the presence of said signal RNA sequence, positive results indicating the presence of said assayed nucleic acid sequence in said sample.

10. A method according to claim 9, wherein the conditions for hybridization in step (e), are lowering of temperature.

11. A method according to claim 1, wherein the detection of the presence of said assayed nucleic acid in the sample is based on the detection of a specific RNA sequence.

12. A method according to claim 1, wherein the presence of the assayed nucleic acid sequence in the sample is based on the detection of an accumulation of RNA molecules following the addition of said transcription reagents.

13. A method according to claim 12, wherein the accumulation of RNA molecules is detected by light absorbance.

14. A kit for use in detecting a nucleic acid sequence in a sample comprising:
a first DNA molecule comprising a double stranded promotor at its 3' end and a single stranded sequence complementary to a 5' end portion of the assayed nucleic acid sequence;
a second DNA molecule comprising a single-stranded sequence complementary to a 3' end portion of the assayed nucleic acid sequence, and further comprising a sequence which can be transcribed into a detectable RNA molecule; and
an RNA polymerase for transcribing said first and second oligonucleiotides;
wherein said detectable RNA molecule comprises (a) a self-replicating signal molecule, (b) the transcripts of said first and second DNA molecules, and (c) a stop sequence to prevent replication of the transcripts of said first and second DNA molecules.

15. The kit according to claim 14 wherein said detectable RNA molecule forms a loop.

16. The kit according to claim 15 wherein the hybridized arms of said loop form a functional promoter.

17. Assay components for selectively amplifying an RNA molecule in a sample, said components comprising:
a first promoter having a single stranded sequence at the 3' end of its non-coding strand adapted to hybridize to the 3' end of said RNA molecule;
a second promoter having a single stranded sequence at the 3' end of its non-coding strand adapted to hybridize to the 3' end of the transcript of said RNA molecule;
ribozymes adapted to cleave any portion of a first or second promoter which is transcribed; and,
RNA polymerase adapted to recognize said first and second promoters and transcribe the sequences downstream thereof.

18. An assay for detecting a nucleic acid sequence in a sample comprising:
a first DNA molecule having a promoter and a 5' end complementary to the 5' end of the assayed nucleic acid sequence;
a second DNA molecule having a single-stranded 3' end complementary to the 3' end of the assayed nucleic acid sequence and 5' end which can be transcribed to an RNA molecule adapted to be selectively amplified by the assay components of claim 17; and
means for detecting said amplified RNA molecule so as to indicate the presence of said assayed nucleic acid sequence in the medium.

19. The method of claim 1, further including a blocker nucleic acid for eliminating the hybridization of a non-perfectly matched nucleic acid sequence, which is contained in an assayed sample, to another nucleic acid sequence forming part of said detection ensemble.

20. The kit of claim 14, further including a blocker nucleic acid for eliminating the hybridization of a non-perfectly matched nucleic acid sequence which is contained in said sample, to another nucleic acid sequence foaming part of said detection ensemble.

21. The assay components of claim 18, further including a blocker nucleic acid for eliminating the hybridization of a nor-perfectly matched nucleic acid sequence which is contained in said sample, to another nucleic acid sequence forming part of said detection ensemble.

* * * * *